(12) United States Patent
Hart et al.

(10) Patent No.: US 8,133,196 B2
(45) Date of Patent: Mar. 13, 2012

(54) INSUFFLATION GAS WARMER AND HUMIDIFIER

(75) Inventors: Charles C. Hart, Summerville, SC (US); John R. Brustad, Dana Point, CA (US); Zoran Falkenstein, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 12/902,890

(22) Filed: Oct. 12, 2010

(65) Prior Publication Data

US 2011/0028890 A1 Feb. 3, 2011

Related U.S. Application Data

(63) Continuation of application No. 11/009,440, filed on Dec. 9, 2004, now Pat. No. 7,811,253.

(51) Int. Cl.
*A61M 13/00* (2006.01)

(52) U.S. Cl. .......................................... 604/24; 604/26

(58) Field of Classification Search .................. 604/113, 604/24, 26
See application file for complete search history.

(56) References Cited

U.S. PATENT DOCUMENTS

| | | | |
|---|---|---|---|
| 524,156 A | 8/1894 | Bachman | |
| 612,158 A | 10/1898 | Cooper | |
| 3,858,572 A | 1/1975 | Binard et al. | |
| 4,315,873 A | 2/1982 | Smith et al. | |
| 4,662,352 A | 5/1987 | Aviles, Jr. | |
| 4,825,863 A | 5/1989 | Dittmar et al. | |
| 5,006,109 A | 4/1991 | Douglas et al. | |
| 5,025,777 A | 6/1991 | Hardwick | |
| 5,042,455 A * | 8/1991 | Yue et al. | 126/263.02 |
| 5,362,310 A | 11/1994 | Semm | |
| 5,381,510 A | 1/1995 | Ford et al. | |
| 5,411,474 A | 5/1995 | Ott et al. | |

(Continued)

FOREIGN PATENT DOCUMENTS

DE 010152513 A1 5/2003

(Continued)

OTHER PUBLICATIONS

European Patent Office, The International Search Report and the Written Opinion of the International Searching Authority, for International Application No. PCT/US2005/040199, mailed Jun. 1, 2006, 14 pages.

(Continued)

*Primary Examiner* — Jackie Ho
*Assistant Examiner* — Michael J Anderson
(74) *Attorney, Agent, or Firm* — John F. Heal

(57) ABSTRACT

An insufflation gas warmer and humidifier apparatus and methods are provided. Insufflation gas is received from a bulky insufflation tubing. Insufflation gas received travels through, in one aspect, a channel or winding flow path, in a passage. The configuration of the passage ensures that the insufflation gas, which travels through the passage, receives sufficient heat and moisture. A humidifying reservoir humidifies the insufflation gas as the insufflation gas is passed to the passage. In one aspect, an oxygenator introduces slight amounts of oxygen into the insufflation gas. A warmer connected to the passage warms the gas in the passage. The warmer, in one aspect, contains a reactive agent that when exposed to air produces heat that is transferred to the passage to warm the insufflation gas within the passage.

13 Claims, 25 Drawing Sheets

U.S. PATENT DOCUMENTS

| | | | |
|---|---|---|---|
| 5,620,440 | A | 4/1997 | Heckele et al. |
| 5,849,005 | A | 12/1998 | Garrison et al. |
| 5,910,106 | A | 6/1999 | Morgan et al. |
| 5,997,498 | A | 12/1999 | De Juan, Jr. |
| 6,068,609 | A | 5/2000 | Ott et al. |
| 6,139,571 | A | 10/2000 | Fuller et al. |
| 6,231,596 | B1 | 5/2001 | Collins |
| 6,309,382 | B1 | 10/2001 | Garrison et al. |
| 6,645,197 | B2 | 11/2003 | Garrison et al. |
| 6,656,160 | B1 | 12/2003 | Johnson et al. |
| H2093 | H | 1/2004 | Warner et al. |
| 7,250,035 | B1 | 7/2007 | Ott et al. |
| 2002/0072700 | A1 | 6/2002 | Mantell et al. |
| 2003/0014004 | A1 | 1/2003 | Day |
| 2003/0028139 | A1 | 2/2003 | Inoue |
| 2003/0163087 | A1 | 8/2003 | Noice et al. |
| 2003/0181857 | A1 | 9/2003 | Blake et al. |
| 2004/0102731 | A1 | 5/2004 | Blackhurst et al. |
| 2004/0254524 | A1 | 12/2004 | Spearman et al. |
| 2005/0107766 | A1* | 5/2005 | Ott et al. .................. 604/500 |
| 2006/0033223 | A1 | 2/2006 | Mantell et al. |

FOREIGN PATENT DOCUMENTS

| | | |
|---|---|---|
| JP | 411178787 A | 7/1999 |
| WO | WO 02/00284 A2 | 1/2002 |

OTHER PUBLICATIONS

International Bureau of WIPO, The International Preliminary Report on Patentability, mailed Jun. 21, 2007, for International Application No. PCT/US2005/040199.

Co-Pending U.S. Appl. No. 11/062,022, filed Feb. 18, 2005. Title: Surgical Access Apparatus and Method.

Co-Pending U.S. Appl. No. 11/680,835, filed Mar. 1, 2007. Title: Gas Insufflation and Suction/Irrigation Tubing.

Co-Pending U.S. Appl. No. 11/868,901, filed Oct. 8, 2007. Title: Method for Manufacturing High Flow Insufflation Needle Stylet.

Co-Pending U.S. Appl. No. 11/383,927, filed May 17, 2006. Title: Surgical Access Apparatus and Method.

Co-Pending U.S. Appl. No. 11/009,440, filed Dec. 9, 2004, Title: Insufflation Gas Warmer and Humidifier.

* cited by examiner

INSUFFLATION GAS WARMER AND HUMIDIFIER

CROSS-REFERENCE TO RELATED APPLICATIONS

This application is a continuation of U.S. patent application Ser. No. 11/009,440, entitled "INSUFFLATION GAS WARMER AND HUMIDIFIER," filed on Dec. 9, 2004, currently pending, which is incorporated herein by reference in its entirety.

BACKGROUND

The present invention generally relates to laparoscopic surgical devices and methods and, in particular, insufflation gas humidifiers and warmers and methods thereof.

Less invasive procedures have been developed for conducting abdominal surgeries through tubular access devices commonly referred to as trocars. These procedures, which call for the placement of the trocar across the abdominal muscle, which defines the abdominal wall, are commonly referred to as laparoscopic procedures. Less invasive laparoscopic surgeries significantly reduce trauma and healing times resulting from the small puncture wounds associated with the trocars, as opposed to the large incisions associated with open surgery.

Laparoscopic procedures or surgeries, however, can be difficult to perform since the abdominal cavity is maintained substantially intact. This decreases visibility of the operative site and also provides a limited volume within which to manipulate instruments. In order to increase this volume as much as possible, the abdominal cavity is typically inflated or insufflated with carbon dioxide or other gas in order to distend the abdominal wall and increase the volume of the abdominal cavity. This insufflation takes place prior to, as well as during, the laparoscopic surgical procedure. Throughout this entire period, the insufflation gas is introduced to the cavity in order initially to distend the abdominal wall and ultimately to replace any escaping gas. The insufflation gas, e.g., carbon dioxide, is typically stored in cylinders under high pressure and released through regulators and valves. As the carbon dioxide expands, it cools and may reach water-freezing temperatures. The expanding gas is also extremely dry, i.e., almost no moisture content.

Introducing cold and dry gas into the abdominal cavity can be problematic. The insufflation gas will reach equilibrium with the surrounding abdominal cavity after it has reached body temperature and 100% relative humidity. The energy to heat cold and dry gas will come from the patient, which may be a significant amount of energy due to the latent heat of vaporization, which is 580 calories per gram of water at 37° C. Over the course of a lengthy surgical procedure 200 liters or more of gas may be used. The peritoneal lining of the abdominal cavity is highly vascularized and secretes a water-based lubricant that acts to protect organs as they slide against each other during normal function. This lining coats the entire abdominal cavity and has a surface area roughly equivalent to the surface area of the patient's skin. Application of cold and dry gas during laparoscopic surgery will severely dehydrate and cool the peritoneal layer and may contribute to postoperative pain and delayed or impaired healing. Additionally, the dry gas may remove the protective moisture of the sensitive abdominal structures, which may cause ileus, adhesions and other problems. Furthermore, the Laparoscopic patient is under anesthetic and lying on a stainless steel table and may therefore be vulnerable to hypothermia due to the aforementioned energy expenditure and/or the introduction of cold gas causing the core temperature of the patient to drop.

Previous attempts to provide solutions included heating insufflation gas at the insufflator. However, a warm gas loses its warmth during passage through the insufflation tubing. The carbon dioxide will be at ambient room temperature after traveling only a few feet through the insufflation tubing. As such, heating the carbon dioxide at the insufflator is ineffective. (See, for example, exemplary test results shown in FIG. 1). Insulated insufflation tubing also shows no appreciable improvement to the distance the carbon dioxide can travel prior to reaching ambient temperature. It becomes apparent that in such cases the carbon dioxide will arrive at the patient at room temperature.

In addition, any device that heats and humidifies the carbon dioxide should also be cost effective. Typical heaters at the insufflators or insulated insufflation tubing are costly or bulky. Such complications do not justify greatly increased expenditures to achieve warm and humid carbon dioxide.

SUMMARY

By adding humidity to the insufflation gas, e.g., carbon dioxide, prior to reaching the patient, at least two favorable results are achieved. First, moisture in the gas greatly increases the heat capacity. This added heat capacity increases the distance through which the gas can travel and not lose all of its energy. (See, for example, exemplary test results shown in FIG. 2). With the fully humidified carbon dioxide at 50° C., the gas can travel at least two feet and be at 37° C. at the access port. This travel distance, however, is dependent on the flow rate and even in combination with insulated tubing is inadequate for delivering warm and humid carbon dioxide through the entire length of typical insufflation tubing, usually about ten feet in length. (See, for example, exemplary test results shown in FIG. 3). Second, adding the humidity to the warm carbon dioxide gas, the peritoneal layer will not be forced to give up any additional water in the form of moisture and thus also not cause the body to liberate the prodigious amounts of energy to provide this moisture.

The present invention, in one embodiment, provides a simple, lightweight, unobtrusive and inexpensive device that warms and humidifies insufflation gases proximal to the entry site or access port. In one aspect of the present invention, an insufflation gas warmer and humidifier apparatus is provided. The insufflation gas warmer and humidifier comprises an inlet arranged to receive insufflation gas, an outlet, a passage, a warmer and a humidifying reservoir. The passage has at least one channel winding throughout an interior of the passage and is connected to the outlet and the warmer is connected to the passage and includes a permeable envelope containing a reactive agent and a surface arranged to transfer heat to the passage. The humidifying reservoir is connected to the passage. In one aspect, the apparatus further comprises sterile fluid and hydrogen peroxide within the humidifying reservoir.

In another aspect of the present invention, an insufflation gas warmer and humidifier apparatus comprises an inlet arranged to receive insufflation gas, an outlet, a passage, a first warmer, a humidifier reservoir, an airtight package and a connecting tube. The passage has at least one convoluted channel extending throughout an interior of the passage and is connected to the inlet and the outlet. The channel has a predetermined geometry in that the insufflation gas received is provided sufficient heat and moisture. The first warmer is adjacent to the passage and includes a permeable envelope containing a reactive agent and a surface. The reactive agent when oxidized produces heat as a by-product and the surface transfers heat to the passage. The first warmer is also operationally arranged to be at a predetermined range of temperatures. The humidifier reservoir is incorporated into the passage and includes a chamber containing sterile fluid and an absorbent pad and arranged to provide moisture. The airtight package encloses the warmer and the connecting tube is connected to the outlet. The insufflation gas warmer and humidifier apparatus in one aspect of the present invention further comprises a second warmer such that the passage is sandwiched between the first and second warmers. In one aspect, the apparatus further comprises an oxygenator connected to the humidifier reservoir.

In yet another aspect of the present invention, an insufflation gas warmer and humidifier apparatus comprises an inlet arranged to receive insufflation gas, an outlet, a passage, a humidifier reservoir and a permeable canister. The passage is connected to the outlet. The humidifier reservoir is connected to the passage and includes a chamber containing sterile fluid housed within the reservoir. The permeable canister is connected to the inlet and the outlet, encompasses the passage and the humidifier reservoir and includes a reactive agent confined within the canister. In one aspect, the humidifier reservoir also includes hydrogen peroxide.

In a further aspect of the present invention, an insufflation gas warmer and humidifier apparatus comprises an inlet arranged to receive insufflation gas, an outlet, means for passing insufflation gas having a predetermined geometry and connected to the inlet and the outlet and means for humidifying the insufflation gas received and connected the means for passing. The apparatus also comprises means for warming the insufflation gas in connection with the means for passing using an oxidized reactive agent disposed within the means for warming and a surface arranged to transfer heat to the means for passing. In one aspect, the apparatus also comprises means for oxygenating the insufflation gas received. In another aspect, the means for passing comprises a passage, means for humidifying comprises a humidifying reservoir, and means for warming comprises a warmer.

In one aspect of the present invention a method of warming and humidifying an insufflation gas comprises receiving insufflation gas, humidifying the insufflation gas, warming the insufflation gas, and supplying the insufflation gas having a predetermined range of temperatures and about 100 percent humidity to an access port via a connector. Warming the insufflation gas further comprises producing heat as a byproduct from a reactive gas mixed with oxygen and transferring the produced heat directly to the insufflation gas. In one aspect, the insufflation gas is oxygenated.

Many of the attendant features of the present invention will be more readily appreciated as the same becomes better understood by reference to the following detailed description and considered in connection with the accompanying drawings in which like reference symbols designate like parts throughout.

DETAILED DESCRIPTION

Figure 1:
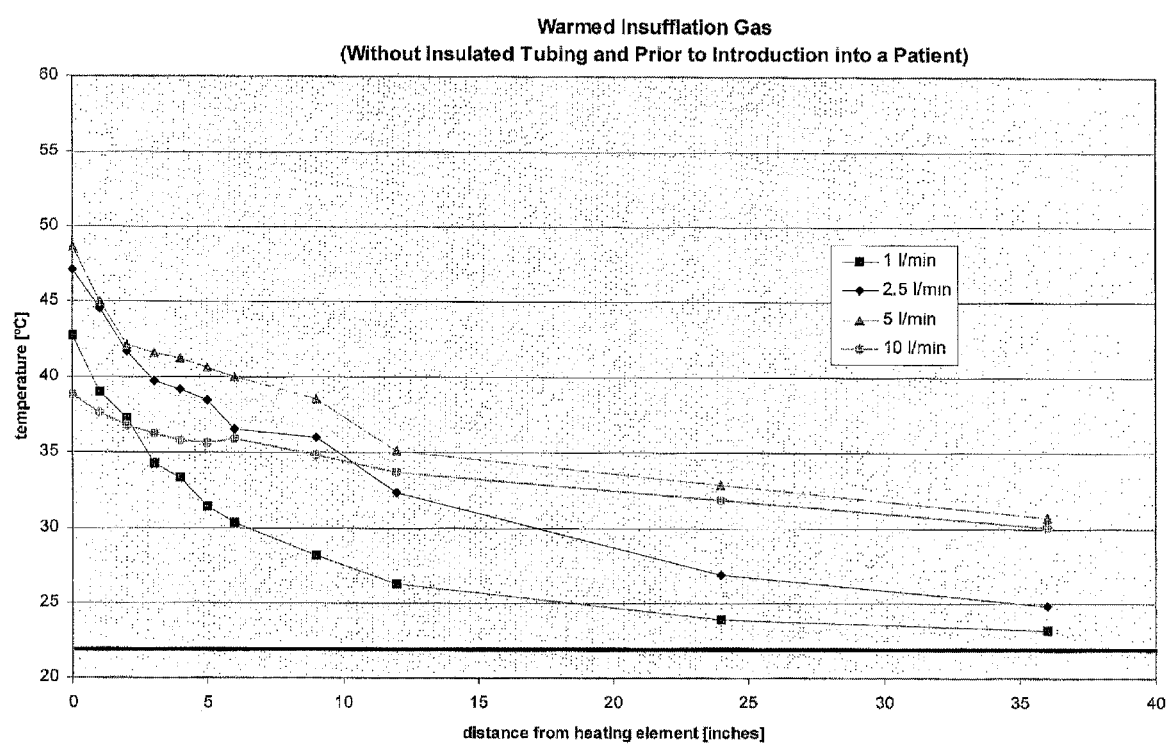
FIGS. 1-3 illustrate exemplary test results of warmed and humidifier insufflation gas in relation to distance, flow rate and temperature relative to various embodiments of an insufflation gas warmer and humidifier in accordance with one aspect of the present invention.
Figure 2:
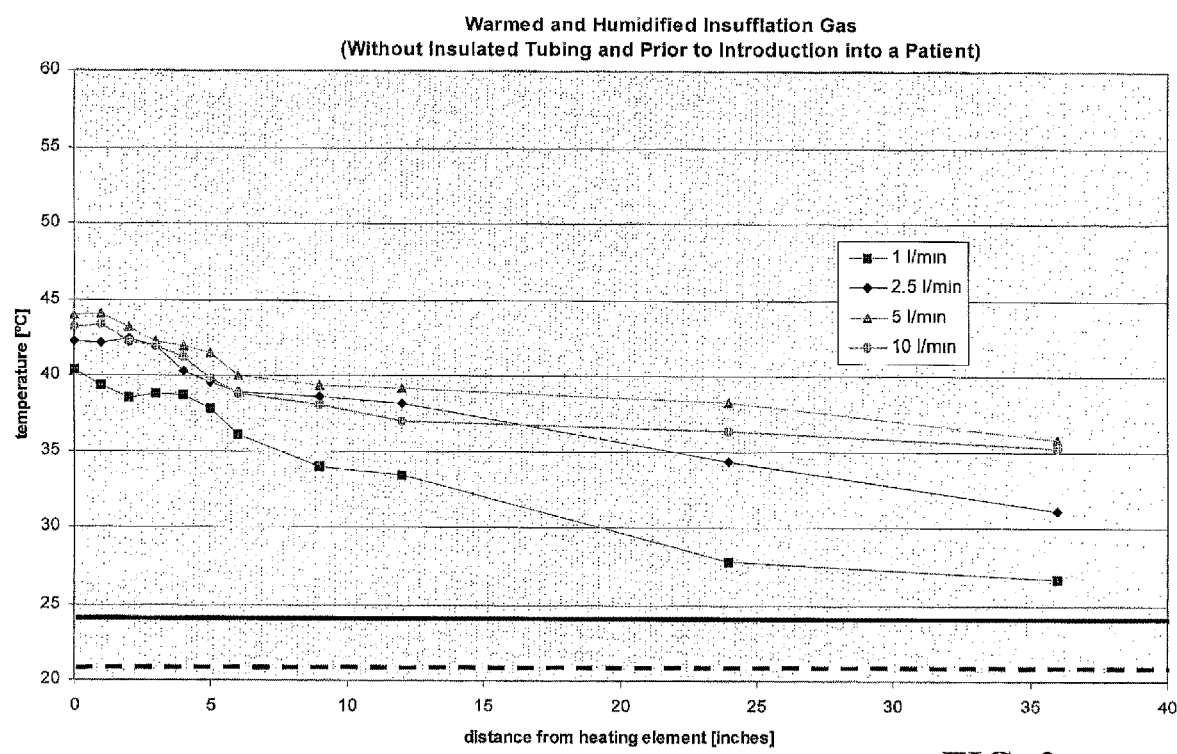
Figure 3:
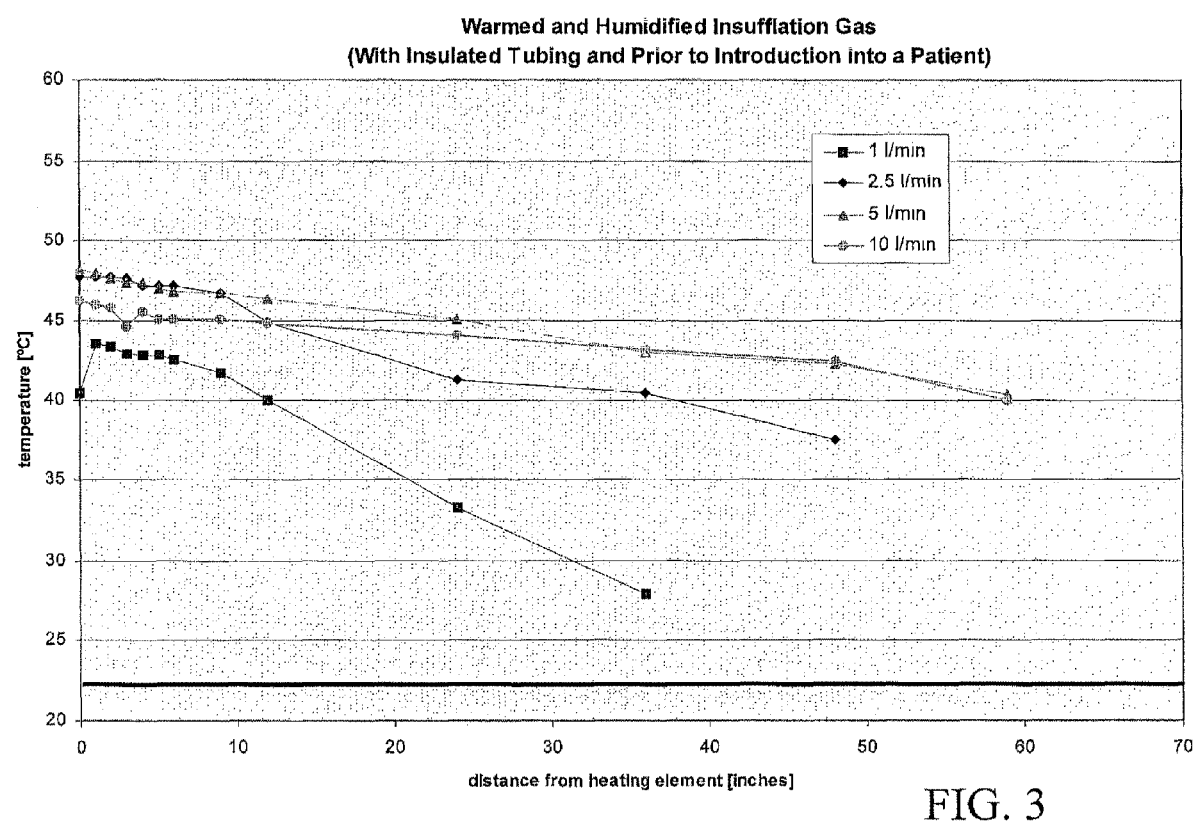
Figure 4:
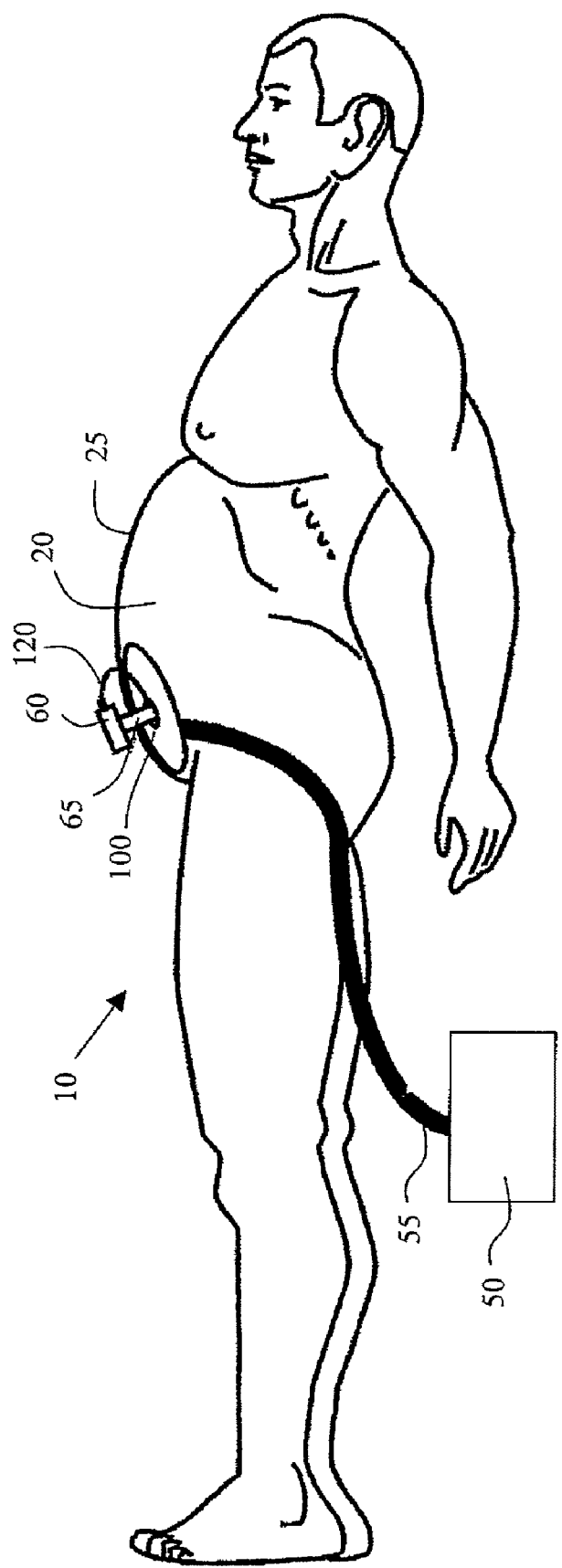
FIGS. 4-5 illustrate various embodiments of an insufflation gas warmer and humidifier in relation to a patient on an operating table in accordance with one aspect of the present invention.
Figure 5:
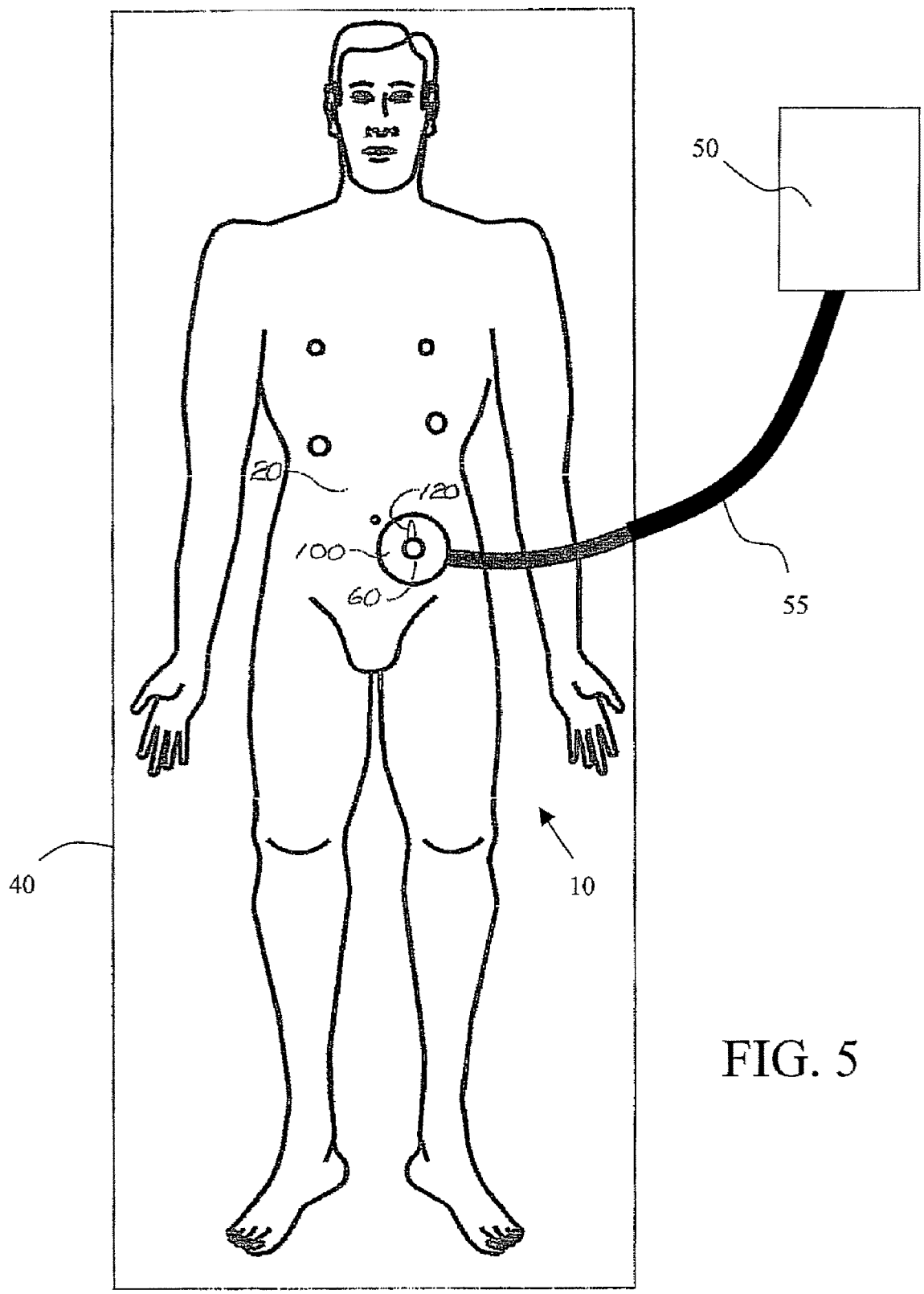

In FIGS. 4-5, a patient 10 in a supine position on an operating table 40 during a laparoscopic surgical procedure is shown to illustrate the present invention. The abdomen 20 of the patient is insufflated with gas from an insufflator 50 through a large bore insufflation needle (not shown). In one embodiment, the insufflation needle has a hollow cylindrical configuration with a sharpened distal tip that is forced through the abdominal wall to provide access to the abdominal cavity through an insufflation channel. An obturator can also be provided with the insufflation needle to inhibit the further penetration of tissue and to extend the insufflation channel from the proximal end of the needle assembly through a channel of the obturator to an outlet port at the distal end of the obturator for communication to regions exterior of the obturator and needle.

Once insufflation is accomplished, access ports 60, 70, and 80, e.g., trocars, are placed through the abdominal wall and into the abdominal cavity. An insufflation gas line or tubing 55 from the insufflator 50 is subsequently transferred from the needle to one of the trocars, e.g., trocar 60. The trocar 60 is used throughout the surgical procedure to regulate and maintain the flow of insufflation gases to the abdominal cavity. The insufflation tubing 55, however, may be bulky and thereby reduce the functionality of the trocar. Also, as noted above, introducing cold and dry insufflation gas can be problematic and if a laparoscope, for example, is inserted through the trocar, cold gas passing the distal end of the laparoscope can cause moisture or fogging on a distal lens of the laparoscope.

A gas warming and humidifying device 100 rests upon the outer skin 25 of the patient and accommodates a portion of a cannula 65 of trocar 60 to pass through the device 100. Insufflation gases pass into the gas warming and humidifying device 100 and subsequently into the trocar 60 through a connecting tube 120. The connecting tube 120 is smaller, e.g., shorter and/or thinner, and/or lighter in weight relative to the insufflation tubing 55. The warming and humidifying device warms and humidifies the insufflation gas that is supplied to the trocar 60 via the connecting tube. As such, the distance traveled by the warmed and humidified gas is relatively small, in one embodiment, about 4 to 10 inches, which minimizes heat loss. As such, the device 100 is positioned proximal to the access port to deliver warmed and humidified gas without interfering with the port or surgical site.

Initially, the insufflation gas is introduced rapidly, e.g., a high flow rate, to insufflate the abdomen. The high flow rate is typically maintained for about two minutes and then slowed. The flow rate can be about zero if the abdomen remains insufflated and rises as insufflation gas is loss or as needed to maintain insufflation of the abdomen. If insufflation of the abdomen is completely loss, insufflation gas is again quickly introduced at a high flow rate. As such, the flow rate at which insufflation gas is introduced into the gas warming and humidifying device 100 varies. The gas warming and humidifying device 100, as will described more fully later, is arranged to provide warm and humidified insufflation gas to a patient at a desired temperature for any combination of varying flow rates for varying durations. Also, with the device 100 being in close proximity to the access port, i.e., delivery of the gas to the patient, the varying flow rates and durations' affects on gas temperature and humidity are minimized.

In one embodiment, the gas warming and humidifying device 100 is substantially circular or oval shaped with an aperture for accommodating the cannula 65 of the trocar 60 to extend there through or for the device to be loosely attached to the cannula. As such, the gas warming and humidifying device 100 does not interfere with the cannula of the trocar 60 and yet remains nearby the trocar 60 thereby increasing the system's efficiency. As such, using insulated or heated insufflation tubing or over heating of the gas is avoided or minimized.

In one aspect, the gas warming and humidifying device 100 also includes an oxygenator. The oxygenator adds a small amount of oxygen to the insufflation gas. As such, the gas warming and humidifying device 100 provides warm, humidified and oxygenated insufflation gas to a patient. Addition of small amounts of oxygen to the insufflation gas has the potential to reduce postoperative pain and ileus and the lower occurrence of access port site infection or hernia.

Figure 6:
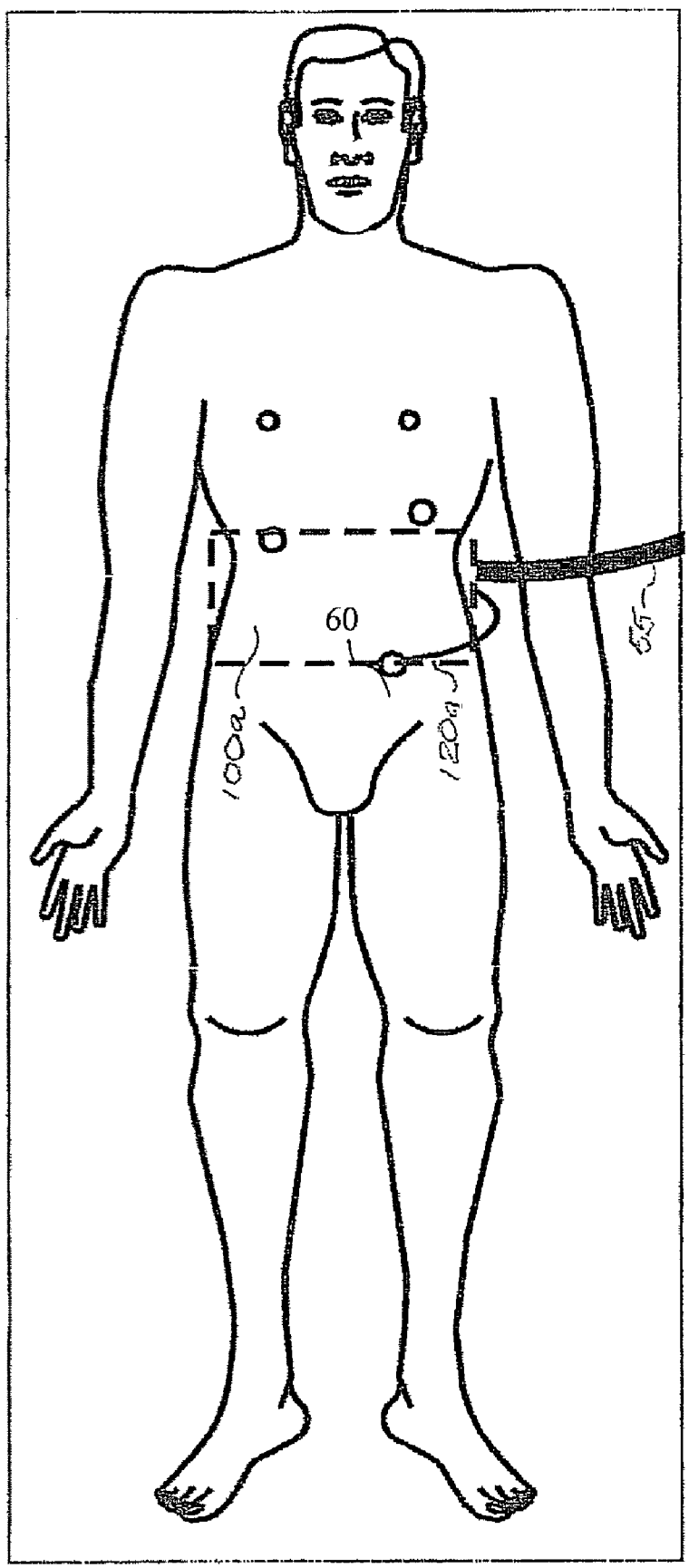
FIGS. 6-7 illustrate various embodiments of an insufflation gas warmer and humidifier between a patient and the operating table in accordance with one aspect of the present invention.
Figure 7:
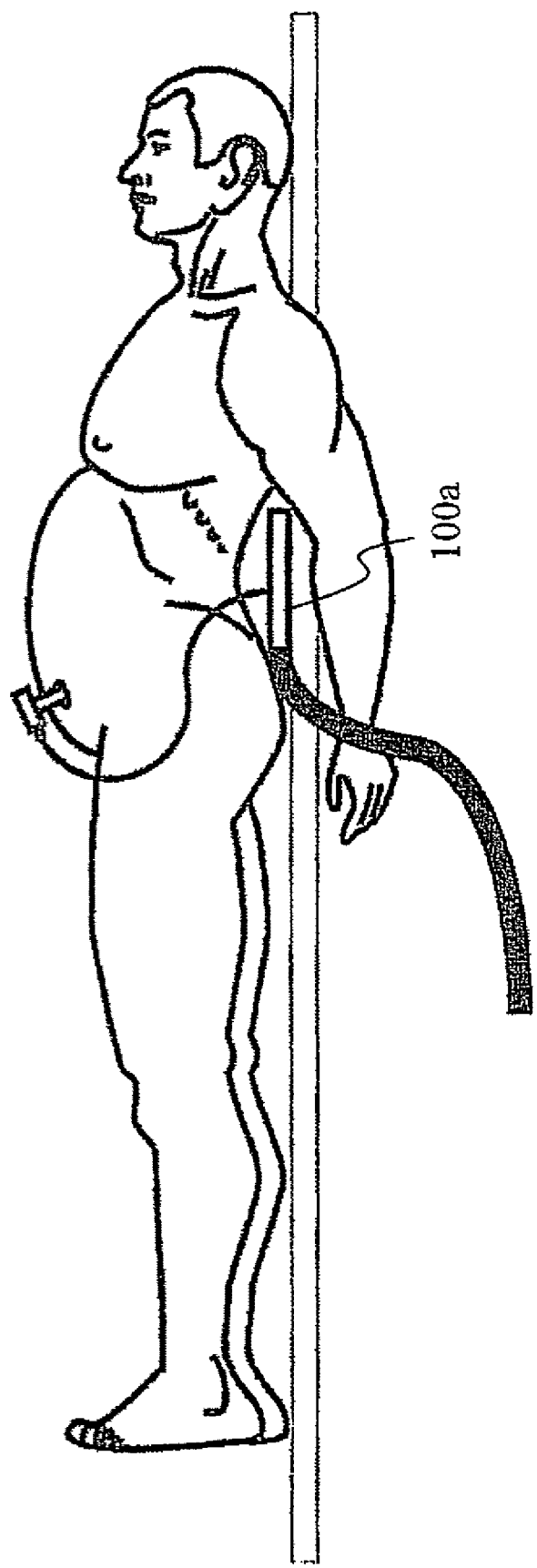

In FIGS. 6-7, other embodiments of a gas warming and humidifying device 100a placed between a patient 10 and the operating table 40 is shown. The insufflation line 55 is connected to the warming and humidifying device 100a. The gas warming and humidifying device 100a is generally rectangular in shape and configured to lie under or over the midsection of the patient. The gas warming and humidifying device 100a, in one embodiment, includes a heat conductive surface arranged to allow releasing or transferring of heat from the device 100a to the patient. The patient may also transfer heat to the device 100a to further warm the insufflation gas. The gas warming and humidifying device 100a is also sized to not interfere with access ports or surgical sites. In one embodiment, the gas warming and humidifying device 100a includes slits, slots or apertures to accommodate and not interfere with the access ports. As such, a trocar may be inserted and the device 100a separated at the slit to allow the device to be opened and slid around the cannula of the trocar. The slit, in one embodiment, is secured closed using adhesive, a Velcro strap, hooks or another simple connector. A connecting tube 120a, which in one embodiment is lightweight, short and/or flexible, connects the gas warming and humidifying device 100a and the trocar 60.

Figure 8:
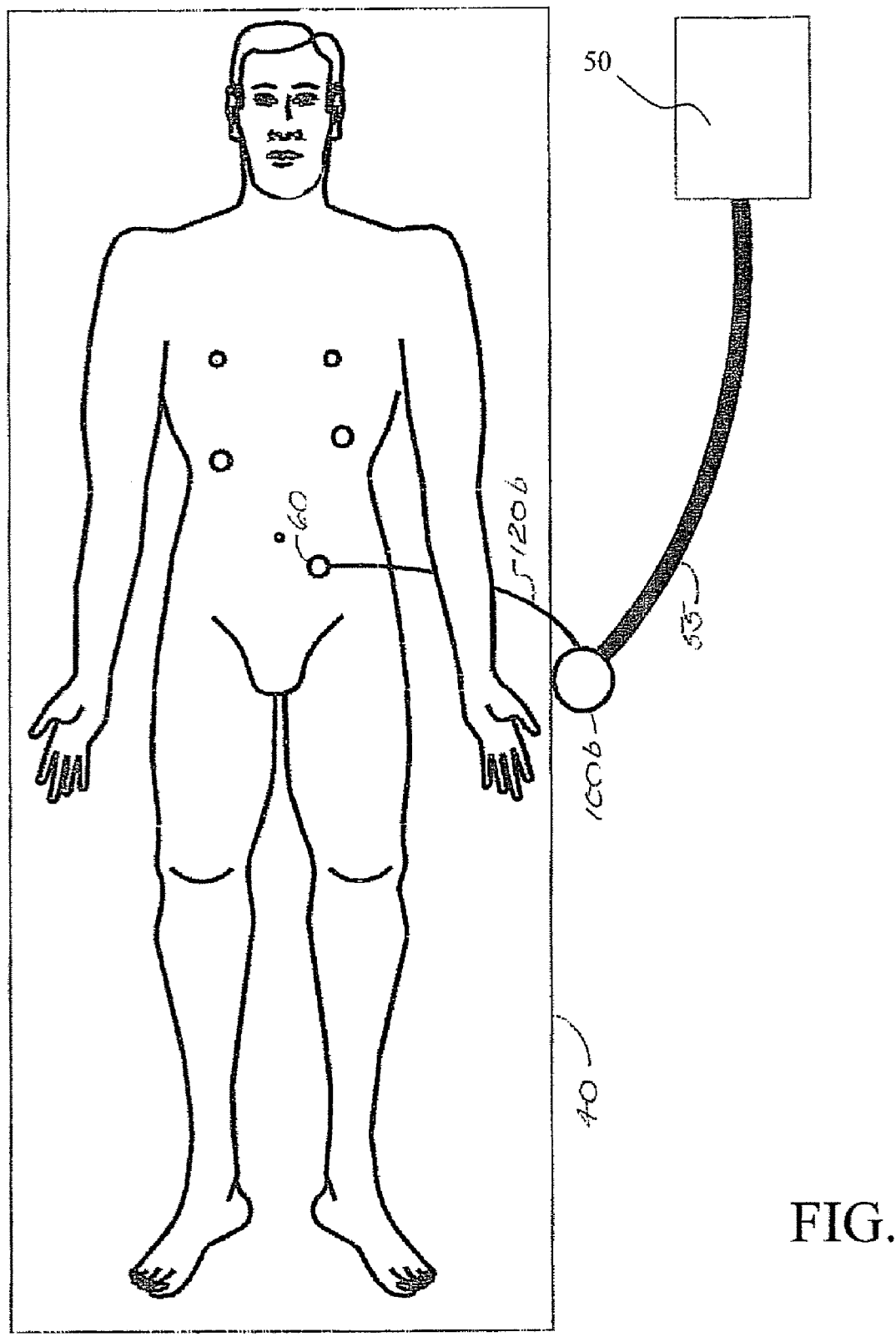
FIGS. 8-9 illustrate various embodiments of an insufflation gas warmer and humidifier attachable to an operating table in accordance with one aspect of the present invention.
Figure 9:
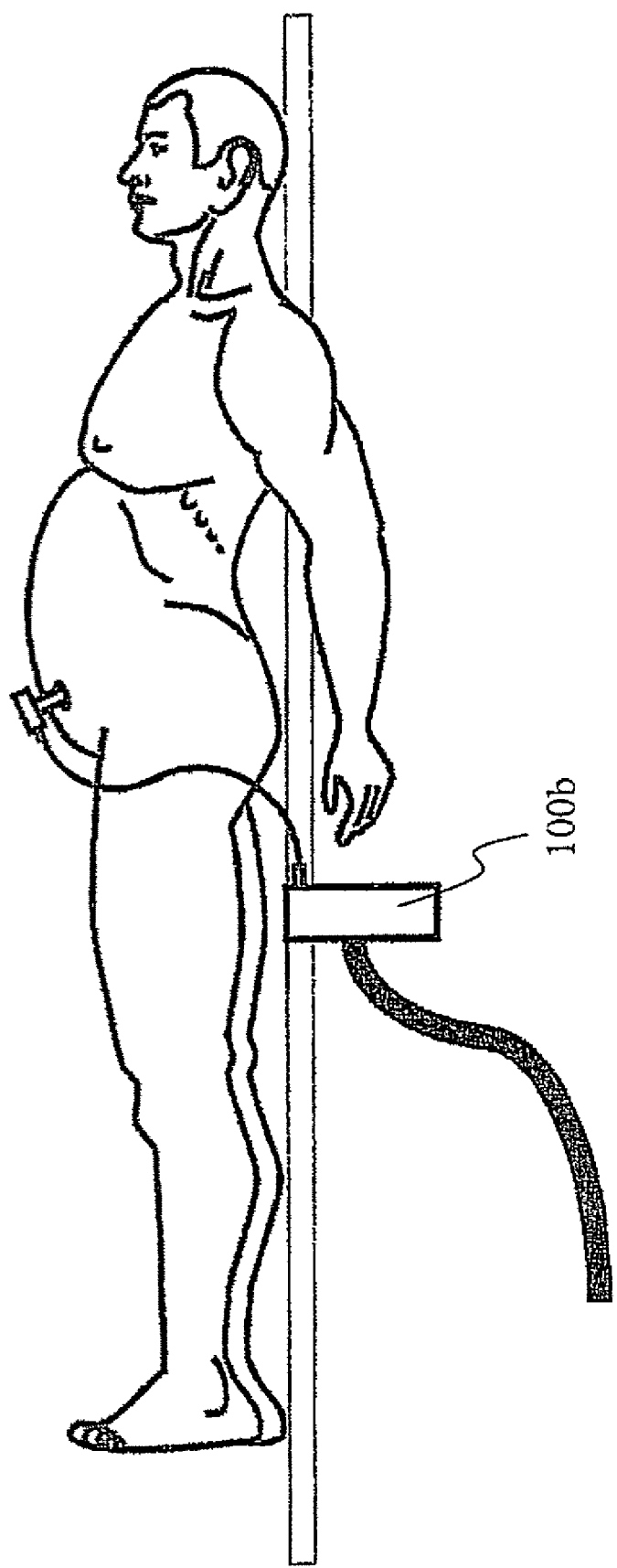

In FIGS. 8-9, a warming and humidifying device 100b is placed upon or attached to an operating table 40. In one embodiment, the device is attached by an anchor, such as a hook, clip, cup, bracket or another type of attachment or support, to the operating table 40. Insufflation gases supplied to the warming and humidifying device 100b are warmed and humidified. A connecting tube 120b, which in one embodiment is small and lightweight, connects the warming and humidifying device 100b to the trocar 60 to pass the gases from the device 100b to the trocar 60. The warming and humidifying device 100b shown is a canister and generally cylindrical or rectangular in shape or otherwise similarly shaped to be unobtrusive.

Figure 10:
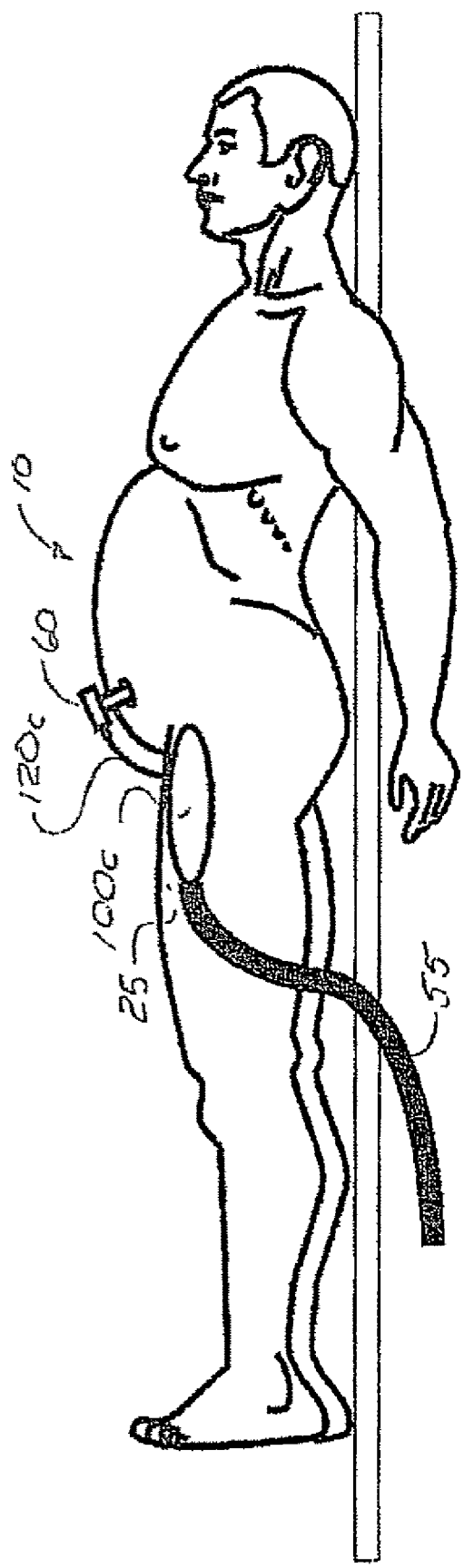
FIG. 10 illustrates one embodiment of an insufflation gas warmer and humidifier positioned on a patient in accordance with one aspect of the present invention.
Figure 11:
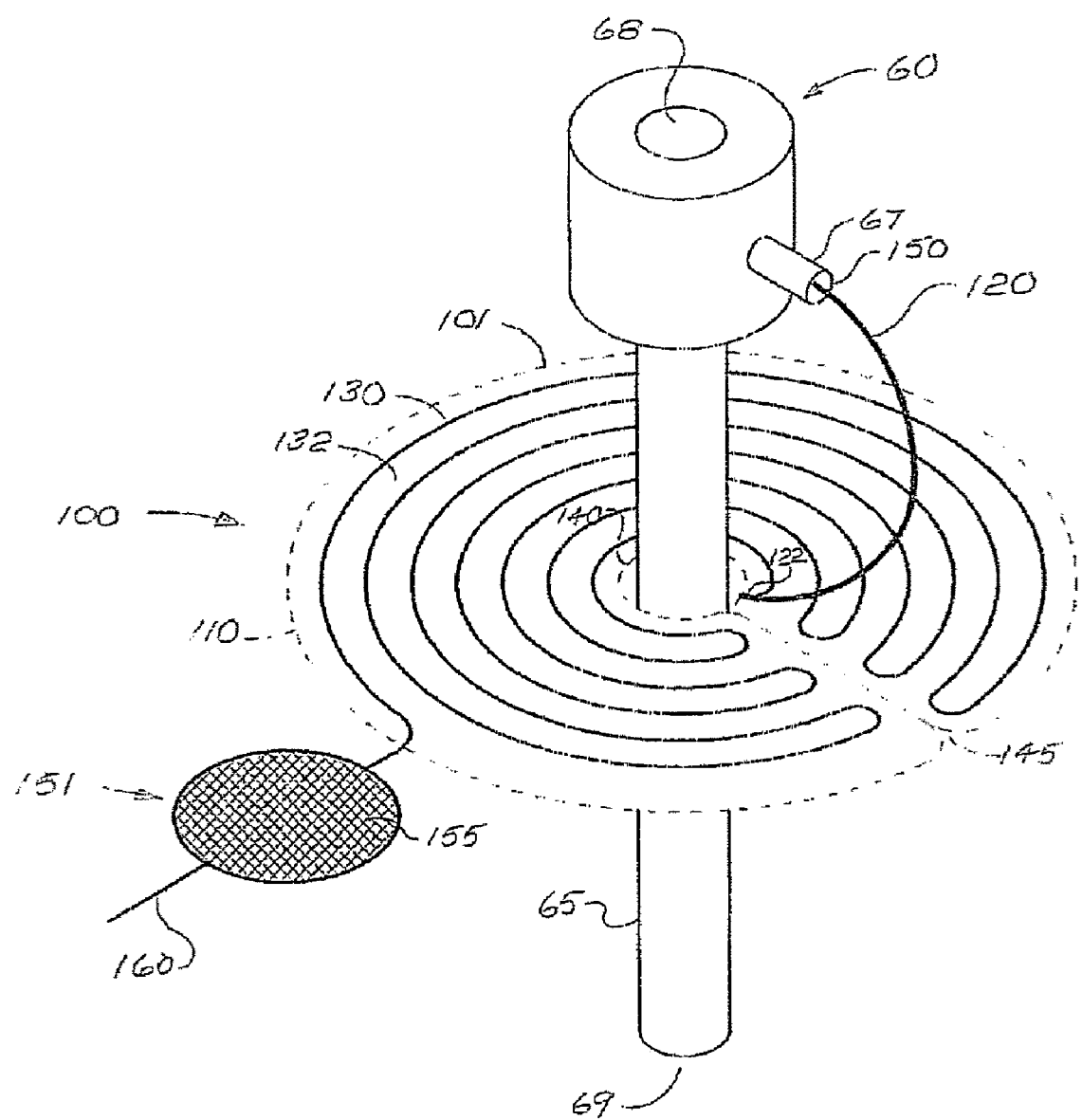
FIGS. 11-14B illustrate various embodiments of an insufflation gas warmer and humidifier in accordance with one aspect of the present invention.
Figure 12:
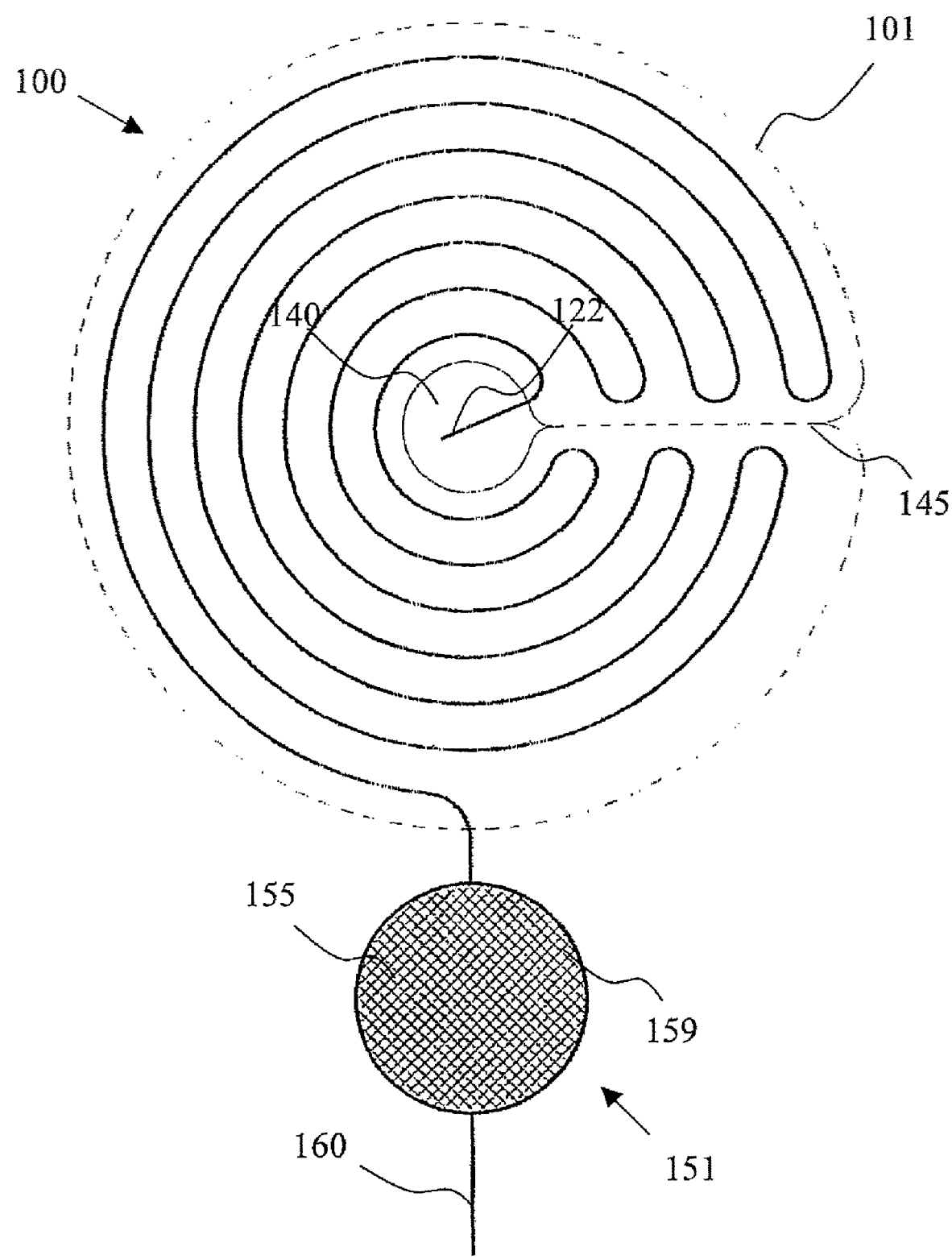
Figure 13:
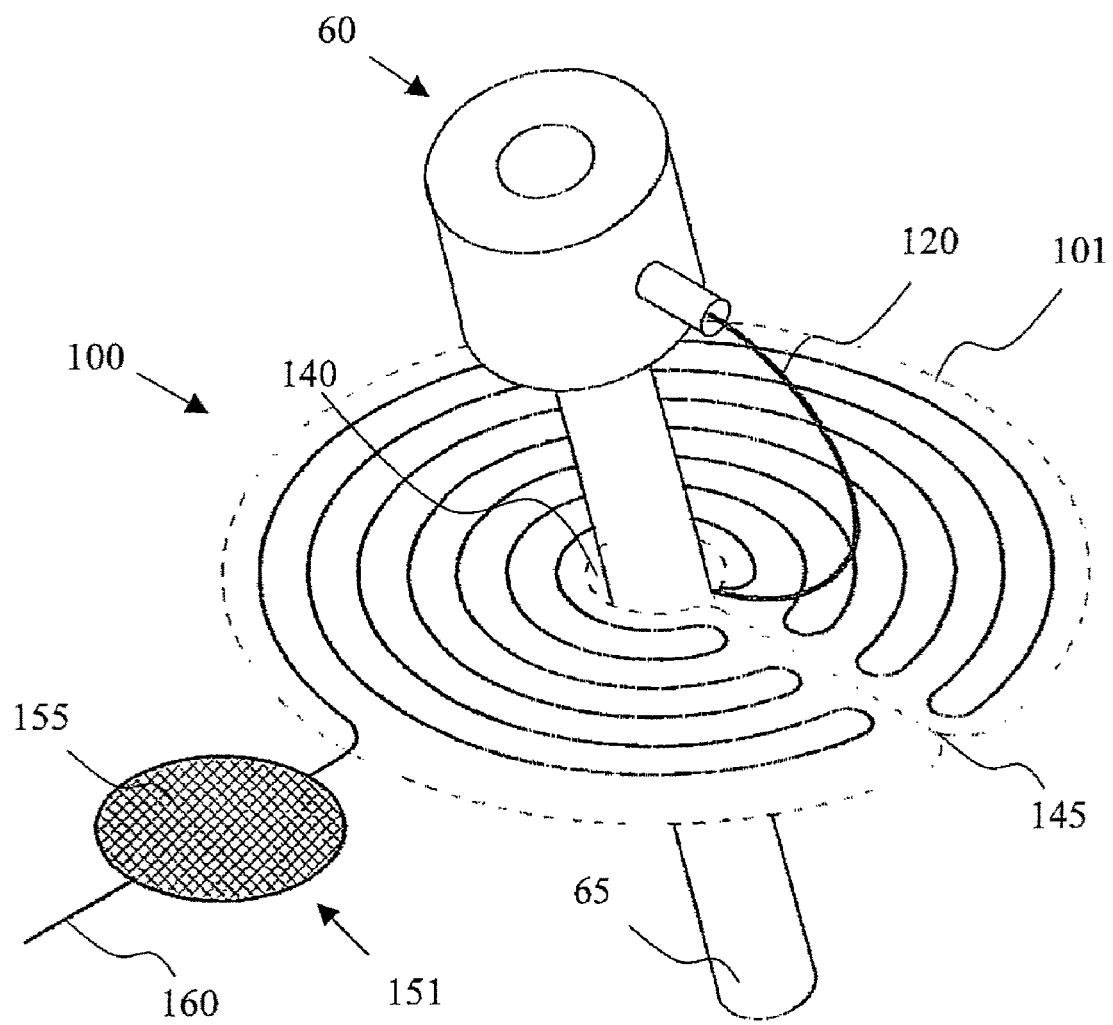

In FIG. 10, a warming and humidifying device 100c is laid upon or attached, e.g., by adhesive, to the skin 25 of the patient 10 and subsequently attached between an insufflator 50 and the trocar 60. A connecting tube 120c that is smaller compared to the insufflation tubing 55 connects the warming and humidifying device 100c to the trocar 60 to pass the gases from the device 100c to the trocar 60. The warming and humidifying device 100c, in one embodiment, includes a protective surface, material lined or otherwise coated that helps to protect a patient's skin from heat emitted from the warming and humidifying device 100c. The gas warming and humidifying device 100c, in another embodiment, includes a heat conductive surface, material or coating arranged to allow releasing or transferring of heat from the device 100c to the patient.

Referring now to FIGS. 11-14B, other embodiments of a gas warmer and/or humidifier device 100 substantially proximal to an access port, e.g., trocar 60, are shown. The circular structure and/or material, e.g., plastic or rubber, of the gas warmer and humidifier 100 encircling the trocar 60 may shield and/or protect the abdominal skin 25 of the patient 10 or surgical site from abrasion as the trocar 60 is manipulated during the surgical procedure (FIG. 13-14B) and yet not interfere with the trocar. A connecting tubing 120 is short and/or lighter relative to the insufflation tubing 55 and extends between the gas warmer outlet 122 and the trocar inlet 67, which also assists in accommodating and not interfering with the surgical site or manipulations of the access port. In one embodiment, a slit 145 traversing the radius of the holding member 101 is provided through which a trocar, for example, may be inserted. Also, the slit 145 allows the holding member 101 to be slid into place or removed from the site without disturbing the access port, e.g., trocar 60.

Figure 16:
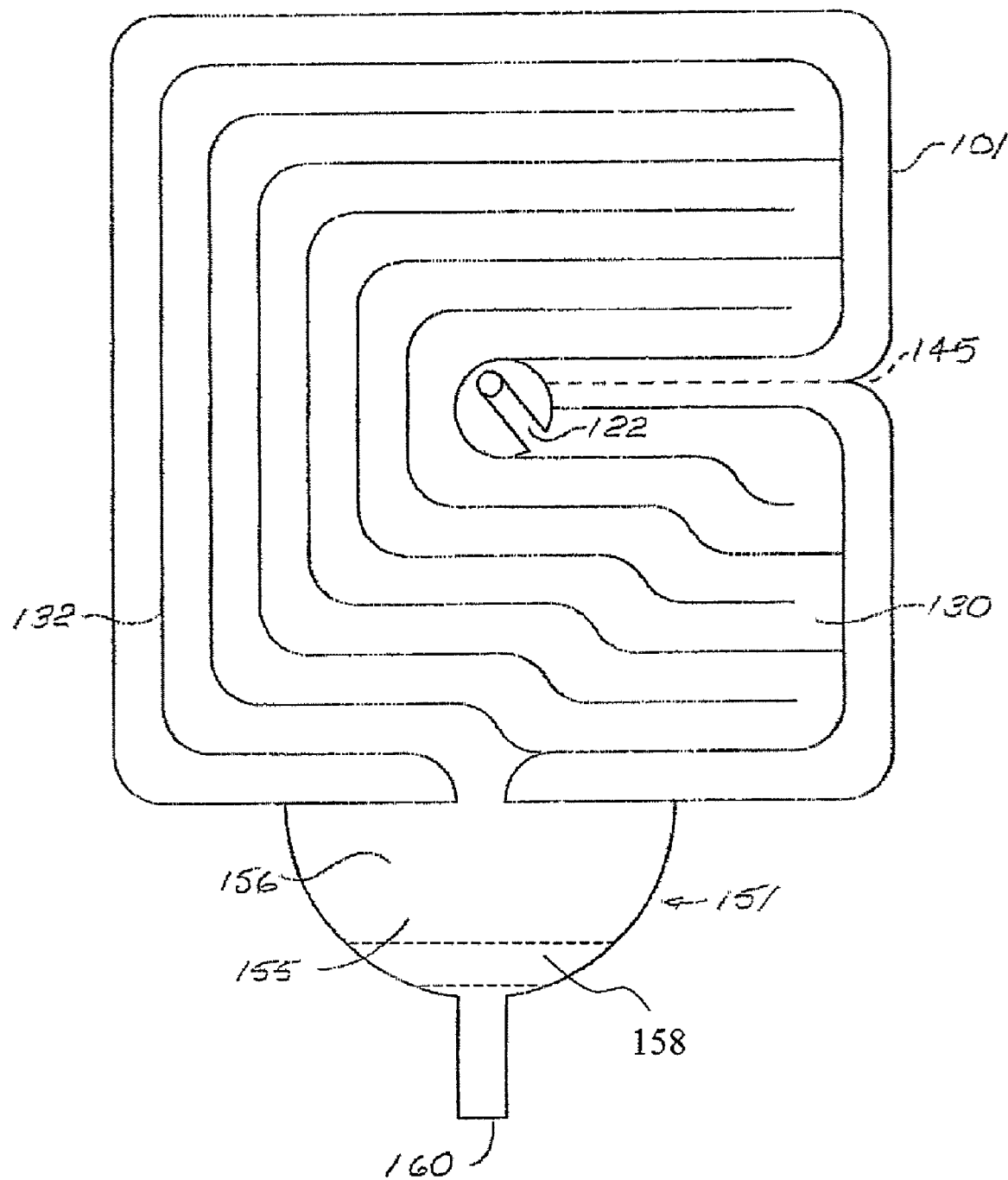
FIG. 16 illustrates one embodiment of an insufflation gas warmer and humidifier with a non-circular pathway in accordance with one aspect of the present invention.

The warming and humidifying device 100 includes a passage 101 having, in one embodiment, an outer portion 110 and an inner portion 132 is shown. The passage 101 is arranged to conduct or pass insufflation gas from the outer portion 110 towards the inner portion 132 of the passage 101. The passage 101 is also arranged generally circular in shape providing or accommodating an aperture or opening 140 through which a cannula 65 of a trocar 60 may be inserted. An inlet valve 67 and/or connection 150 are provided with the trocar 60 to communicate with the passage 101. In one embodiment, that passage 101 is a labyrinth of channels or a convoluted channel 130. An outlet 122 is provided at the opposite end of the labyrinth or channel 130 to transmit the insufflation gas to the inlet 67 of the trocar 60. A non-circular embodiment of the passage 101 is shown in FIG. 16.

The channel is configured to provide that the insufflation gas travels within the passage 101 for a predetermined distance/volume regardless of the gas' flow rate. At a high flow rate, for example, when the abdomen is first insufflated, the insufflation gas travels through the channel 130 rapidly. Once introduced into the channel 130 the gas is heated or warmed by the device 100. The gas continues to be warmed/humidified as it travels through the channel 130 to the outlet 122. The geometry of the channel 130, e.g., length, volume, etc., ensures that the gas will have sufficient energy and moisture transferred to it even if it is moving rapidly which ensures that the gas is warmed/humidified at a predetermined temperature and humidity point or range prior to exiting at the outlet 122. At a low flow rate, for example, when the insufflation is being maintained, the insufflation gas moves slowly if any through the channel 130. Since the gas is moving slowly, the gas is warmed and humidified as it travels and thus the geometry of the channel 130 has a reduced affect on the warming/humidifying of the gas prior to exiting at the outlet 122. However, slowly moving gas may allow the gas to cool after exiting the outlet 122 and prior to the inlet of the trocar 60 or introduction into the patient, for example, as the gas slowly moves through a connecting tube to the trocar. As such, the close proximity of the device 100, outlet 122, to the access port or delivery to the patient minimizes distance/time in which the gas can cool. Also, the amount of gas that may cool in the connecting tube is small due to the small length of the connecting tube.

Figure 14A:
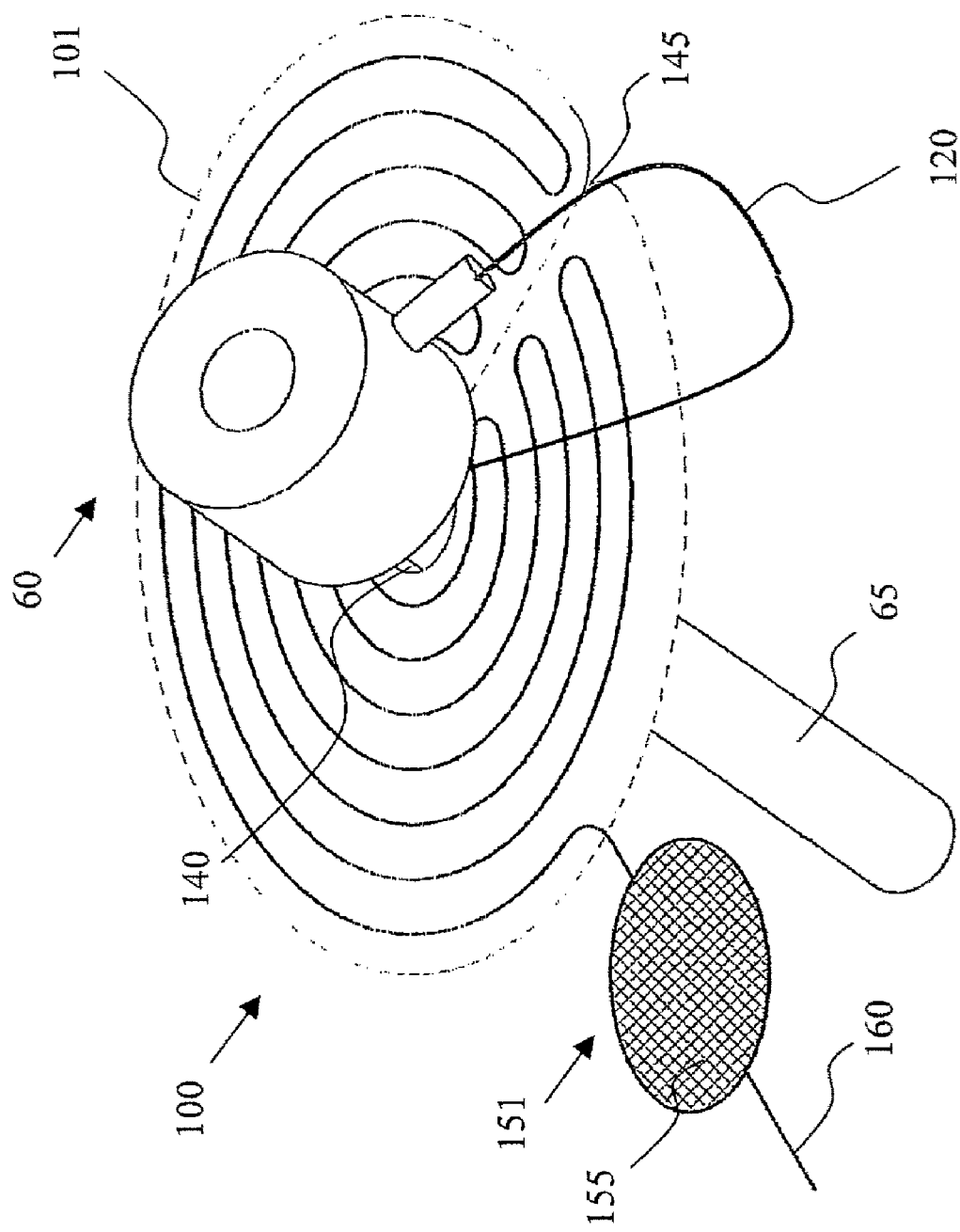
Figure 14B:
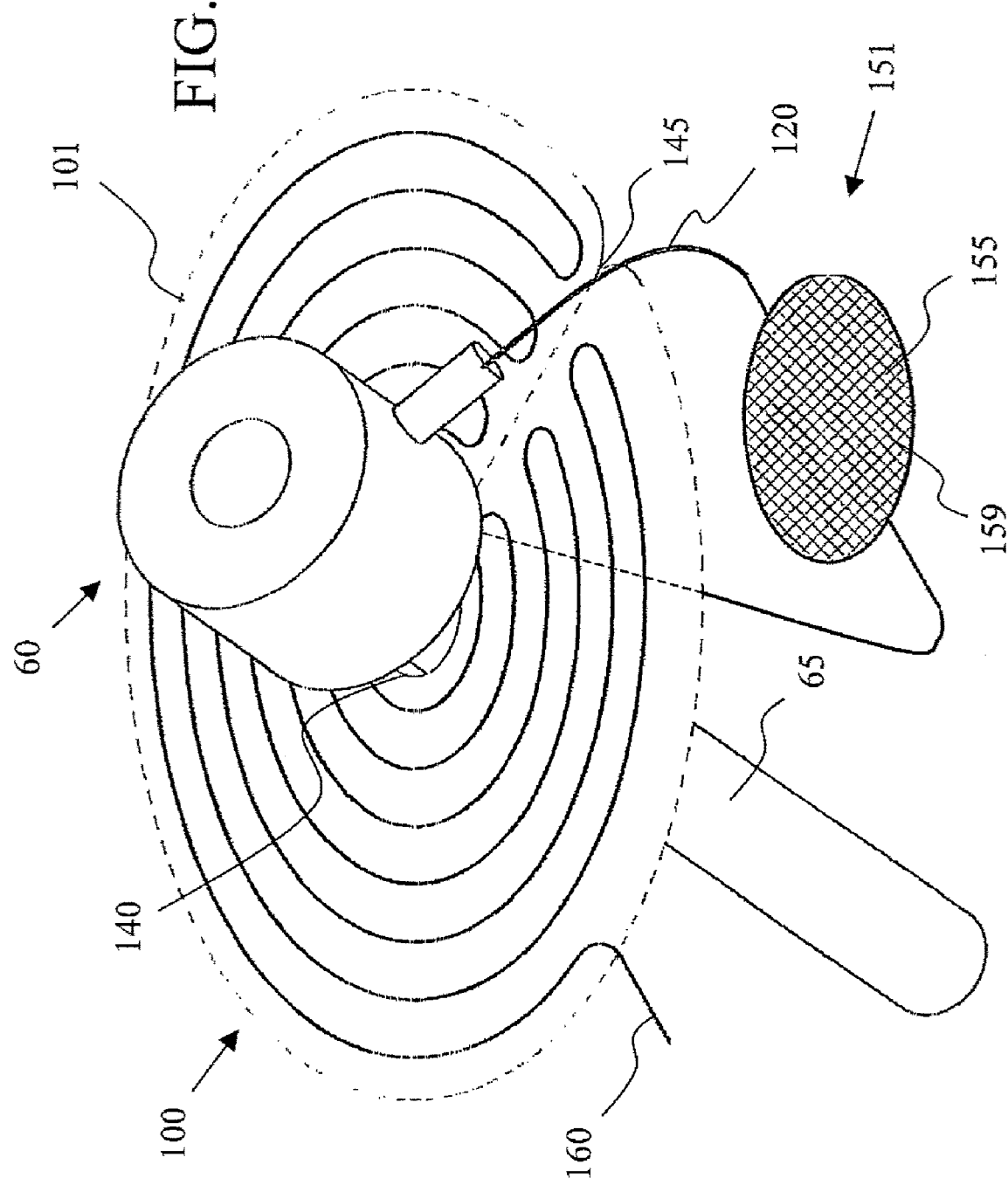
Figure 15A:
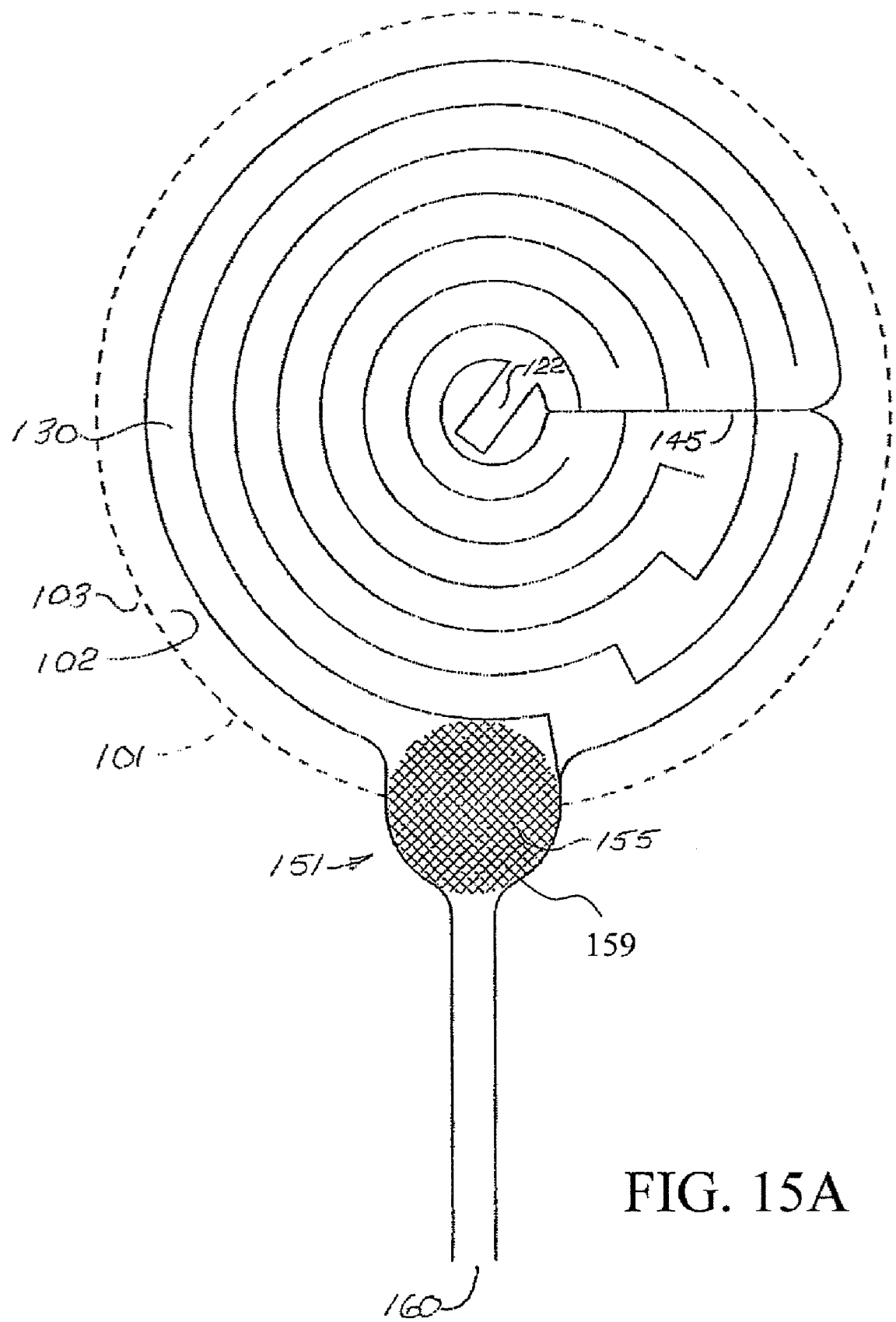
FIGS. 15A-B illustrate various embodiments of an insufflation gas warmer and humidifier with a humidifier reservoir incorporated into the pathway in accordance with one aspect of the present invention.
Figure 15B:
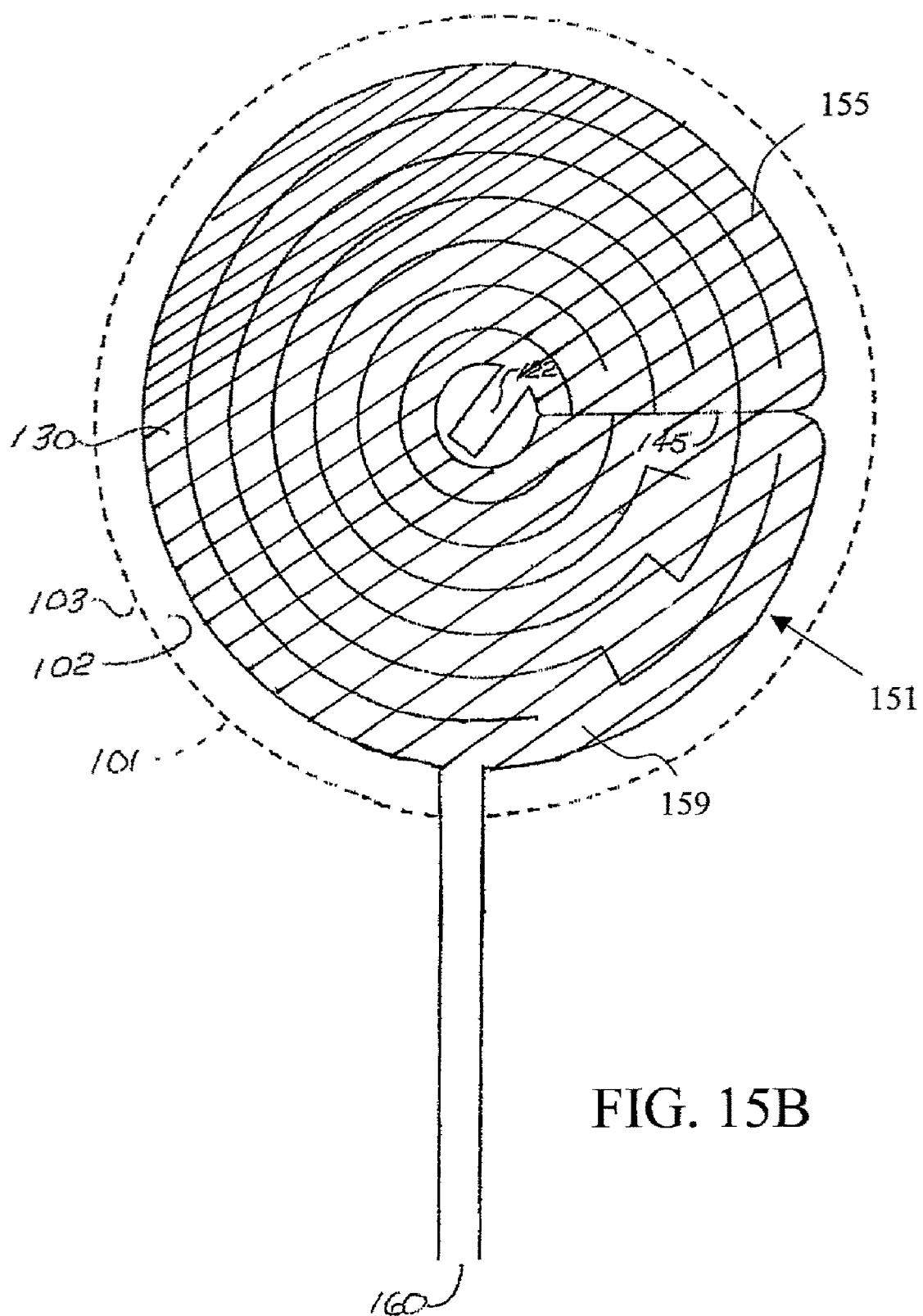

In one embodiment, a humidifying reservoir 151 is placed at the inlet 160 before the passage 101. In another embodiment, a humidifying reservoir 151 is placed at the outlet before the connecting tube 120 (FIG. 14B). The reservoir 151 holds sterile fluid through which the insufflation gas passes. An absorbent foam or fabric 155 is also contained within the reservoir 151 to assist in increasing the moisture in the insufflation gas as the gas passes through the reservoir into the passage 101. In one aspect of the invention, hydrogen peroxide 159, which liberates oxygen, is also included with the absorbent fabric 155. The reservoir 151 in various embodiments are also substantially integrated into the passage 101, as shown in FIGS. 15A-B.

In one aspect of the present invention, a gas conducting structure or passage 101 may be formed by sealing two layers 102 and 103 together to form multiple channels or a single convoluted channel 130. Insufflation gas introduced through the inlet 160 passes through the channel 130 to reach outlet 122. As the gas passes through the channel 130, the gas travels within the passage 101 for a specific distance. In other words, the configuration and/or size of the channel 130 substantially determine the distance through which the gas travels within the passage, holder or holding section 101.

Figure 17:
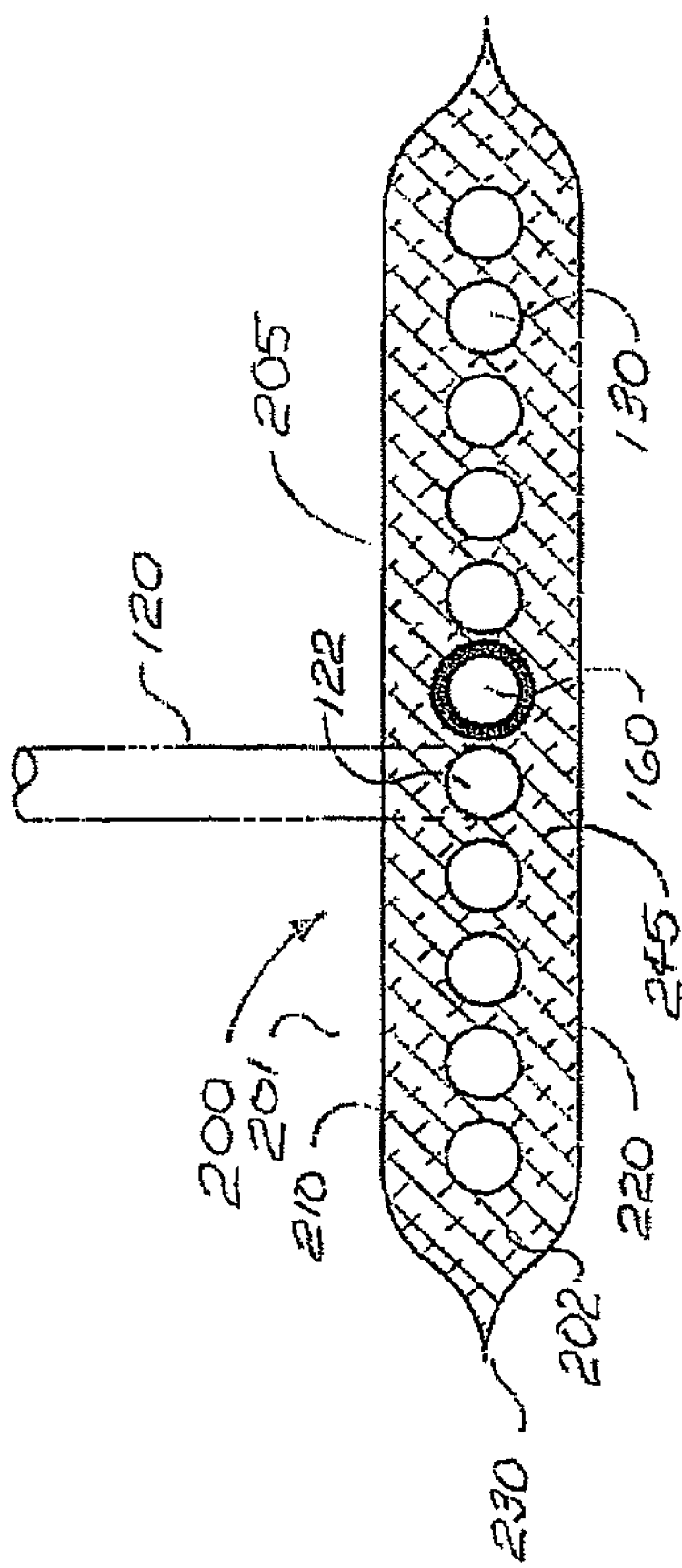
FIG. 17 illustrates one embodiment of an insufflation gas warmer and humidifier with a pathway incorporated or encompassed by a warmer in accordance with one aspect of the present invention.

A warmer or warming member, e.g., warmer 200, is also associated with the passage 101 in one embodiment of the present invention as shown in FIG. 17. In one aspect, one or more warming members may be placed upon one or both sides of the passage 101. The warmer warms the gas residing or traveling within the passage or holding member 101 during the residence or travel time, i.e., the duration or distance in which the gas resides or travels, within the passage 101. In one embodiment, the passage 101 is placed, e.g., sandwiched or laminated, between two warming members. Surfaces, e.g., surfaces 210 and/or 220, on the warmers contact the passage 101 and/or the reservoir 151 to provide a direct contact to transfer heat to the passage 101 and reservoir 151. In another aspect, the passage 101 is placed within a heating member 200 or a coiled or folded length of tubing to provide channels 130 are placed within the heating member 200.

The warming member 200 also includes a chemically reactive envelope 205. Oxygen or moisture exposure of the contents 245 of the envelope 205 causes a chemical reaction within the envelope 205. In one embodiment, the contents include iron powder, charcoal carbon and vermiculite. As a result, heat is produced. In one embodiment, the heat produced is about 50° C. lasting for about three to four hours. The flowing gas within the passage 101 absorbs the heat from the warming section or member 200. The sterile fluid within the reservoir 151 also absorbs the heat from the warmer or warming member 200. Therefore, the insufflation gas from inlet 160 that passes through the reservoir 151 is humidified.

In one embodiment, the warming member 200 is sealed in an airtight package for storage. When the airtight package is opened, oxygen is introduced to the composition of materials or contents 245 of the envelope 205 that oxidize and produce heat as a by-product. The heat generated is sufficient to raise the temperature of insufflating gases without creating potential harm or interference. Once the airtight package in which the warmer 200 is stored is opened, the heat reaction provides adequate warming for several hours. In one embodiment, the warmer surfaces 210 and/or 220 are coated, lined or otherwise made from material to provide a protective portion or surface to inhibit the transfer of heat away from the passage 101 or towards a patient. In another embodiment, the warmer surfaces 210 and/or 220 are coated, lined or otherwise made from material to provide a portion or surface to also permit the transfer of heat away from the passage 101 or towards a patient.

In one embodiment, the heating member 200 includes an air permeable envelope, bag or similar structure 205 that allows a predetermined volume of air to move from the outside of the envelope 205 to the inside of the envelope 205. The air carries sufficient oxygen to cause a reaction with the contents 245 of the heating member 200. The contents 245, in one embodiment, include iron, salt and other materials that generate heat by reacting with incoming oxygen. However, the amount of heat generated or temperature of the envelope 205 does not exceed a predetermined temperature point or range, e.g., about 50° C., to cause potential harm. As such, expensive and/or cumbersome measuring and monitoring equipment may not be needed. Also, overheating of the insufflating gases for transport through the length of tubing 55, which is often long, can be avoided.

The insufflation gas, e.g., carbon dioxide, is humidified early in the journey through the passage 101. For example, the reservoir 151 is provided at or near the inlet 160 of the passage 101 such that insufflation gas passes through the reservoir 151 prior to passing through the channels 130. The insufflation gas, in another embodiment, is humidified throughout the journey through the passage 101. For example, the reservoir 151 incorporated or otherwise merged with the channels 130 of the passage 101. The reservoir 151 is provided at or near the outlet 122 of the passage 101 such that insufflation gas passes through the reservoir 151 after passing through the passage

101. The reservoir 151, in one aspect of the invention, includes a chamber or pouch 156 fitted with an absorbent material 155, such as a porous or open celled sponge, foam, cotton, fabric or other material. In one aspect of the invention, the absorbent material 155 also includes sterilized water. In another aspect of the invention, hydrogen peroxide 159, which liberates oxygen, is also included with the absorbent material 155. As such, humidified, oxygenated and warmed carbon dioxide flows into the abdominal cavity. With the passage 101 being proximal to the access port, trocar 60, cooling or the loss of heat of the gas is minimized. The loss of heat of the gas may be significant if the heated gas first travels through the insufflation tubing 55 prior to being provided to the trocar 60.

In various embodiments, oxygen is supplied or provided to the insufflation gas by other similar chemicals or chemical reactions as using hydrogen peroxide. In other embodiments, oxygen is provided using a small pressurized reservoir of oxygen or a filter unit 158 filtering and allowing a small amount of room air into the reservoir or at other various locations in various embodiments of the insufflation gas warmer and humidifier device or insufflator, e.g., at the insufflator, along the insufflation tubing, the connecting tubing, etc. (e.g., FIG. 16). In one aspect of the present invention, the filter used for the carbon dioxide, the insufflation gas, can also be used for the introduced room air or oxygen. In one embodiment, the filter unit includes a 0.2/0.3 micron filter. The amount of oxygen introduced is very slight to avoid any potential volatility with the mixing of gases or undesired reactions.

Figure 18:
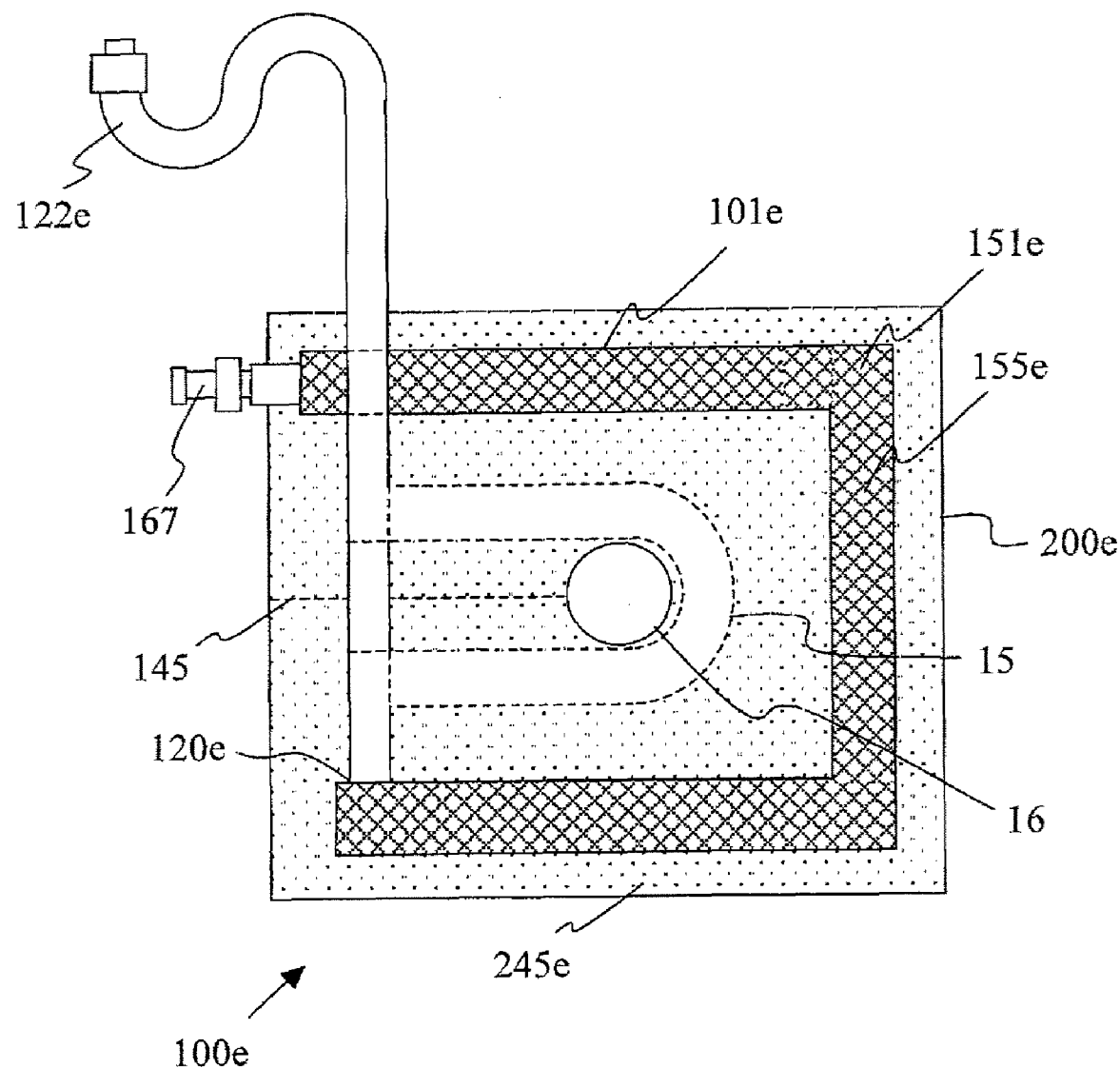
FIG. 18 illustrates one embodiment of an insufflation gas warmer and humidifier with a passage incorporated or encompassed by a warmer in accordance with one aspect of the present invention.

A further embodiment of an insufflation gas warmer and humidifier device 100e, similar to the previously described devices, is shown in FIG. 18. Insufflation gas from the insufflator 50 is supplied to an inlet 167. The insufflation gas passes through a passage 101e incorporated or embedded with a humidifier 151e. In one aspect, the humidifier 151e includes an absorbent pad or towel 155e incorporated within the passage 101e with sterile fluid and, in one embodiment, with an oxygen-introducing chemical. In this and various embodiments, about 10 cc of sterile fluid or sterile water is utilized. The passage 101e is attached or embedded between a warmer 200e that includes contents 245e. In one embodiment, the passage 101e and/or humidifier 151e includes a respective contacting surface arranged to allow the transfer of heat from the contents 245e to the respective components. In one aspect, the warmer 200e includes a permeable envelope including contents 245e and encases passage 101e and humidifier 151e. As such, the insufflation gas from inlet 167 are humidified, warmed and in one aspect oxygenated. The gas exits via outlet 120e and is provided to a valve/cannula or patient via connecting tube 122e.

In one aspect, the connecting tube 122e or passage 101e includes a channel 15 and/or winds around an aperture 16 and a slit 145 to accommodate a cannula and not interfere with an access port. In one aspect, the connecting tube 122e does not intersect the passage 101e to accommodate a cannula, slit 145 and thus not interfere with the access port. The intersection of the connecting tube and the passage 101e in one embodiment allows for a secure arrangement of the connecting tube to the device. In one embodiment, the connecting tube 122e is smaller and lighter than the insufflation tubing from an insufflator. In one embodiment, a separate filter unit allowing the intake of room air or an oxygenator is provided to oxygenate the insufflation gas. In another aspect, the warmer includes heating elements or coils energized to provide sufficient heat to warm the insufflation gas to supplement or used in place of the heat transferred by the contents 245e.

Figure 19:
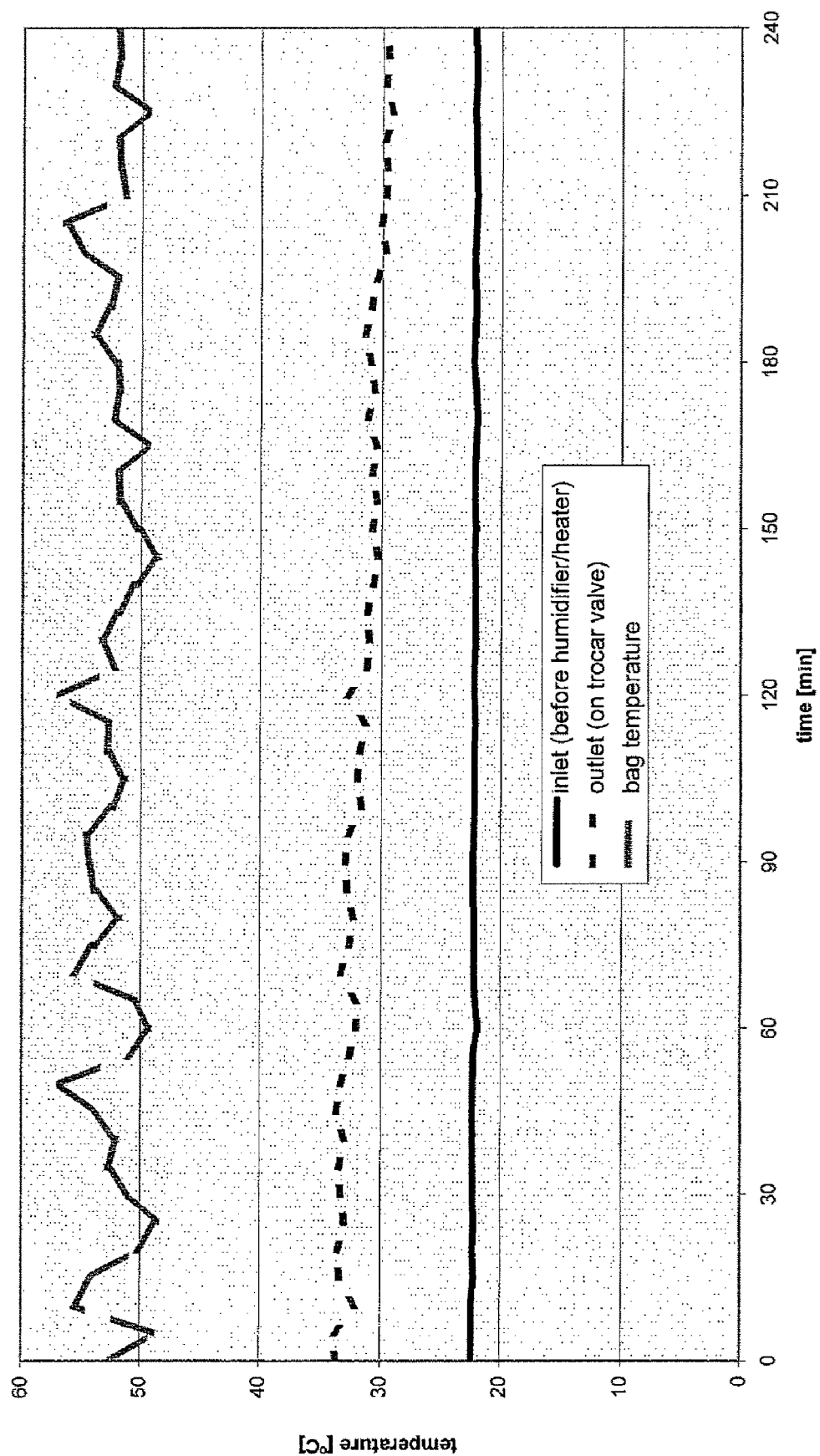
FIG. 19 illustrates an exemplary test result of one embodiment of an insufflation gas warmer and humidifier in accordance with one aspect of the present invention.

FIG. 19 illustrates exemplary test results of insufflation gas warmed and humidified by one embodiment of the above described humidifying and warming device in accordance with one aspect of the present invention. As shown, a warmer ranging in temperature from about 50° C. to 55° C. transfers heat to the humidified gas causing the gas introduced to the patient to be about 30° C. to 35° C. throughout a typical procedure, e.g., about 240 minutes. If the flow rate is varied from 0 to 40 L/min, for example, for low flow rates, e.g., 1 L/min, the lowest range of temperatures of the insufflation gas will be about 30° C. to 35° C. and for moderate flow rates, e.g., 2.5-5 L/min, the range of temperatures of the insufflation gas will be closer to the temperature of the warmer, e.g., about 50° C. to 55° C. However, the insufflation gas will not exceed the temperature of the warmer and thereby not cause any undesired affects.

The temperature of the gas as it arrives at the patient is partly a function of the flow rate of the gas. At low to moderate flow rates, the insufflation gas travels along a passage a predetermined distance (with a predetermined volume) and thereby resides within the passage for sufficient time to warm the gas by heat being transferred to the passage from the warmer. However, as the gas is no longer being warmed, e.g., along a connecting tube, the gas loses its warmth as heat is lost. The gas traveling through the connecting tube at a low flow rate cools or loses heat prior to being introduced into the patient. The slower moving gas cools longer resulting in lower temperatures, e.g., about 30° C. to 35° C., versus more moderate moving gas having higher temperatures, e.g., about 50° C. to 55° C. Thus, at very low flow rates, the long residence time of the gas in the heater/humidifier ensures that the gas is heated to the maximum temperature of the device. The low flow rate, however, also maximizes the travel time of the gas from the device to the patient and thus maximizes the amount of energy liberated during transit causing the gas to arrive at the patient at a lower temperature.

For high flow rates, e.g., about 10 L/min to 40 L/min, the range of temperatures of the insufflation gas will be in a mid-range or lower, e.g., about 40° C. to 45° C. to about 30° C. to 35° C. At high flow rates, the insufflation gas travels along a connecting tube quickly and thereby allows less travel time for the gas to cool, prior to the introduction into the patient. However, at increased or high flow rates, the insufflation gas quickly travels through a passage a predetermined distance (with a predetermined volume) and thereby resides within the passage for a reduced amount of time to warm the gas by heat being transferred to the passage from the warmer. Additionally, in one embodiment, the increased or higher flow rate also includes a higher volume of gas being introduced into the sterile fluid. This increased volume also reduces the transfer of heat to the gas and may even cause the fluid to cool. As such, the high moving gas is allowed to heat and also cool less resulting in lower temperatures, e.g., about 30° C. to 45° C., versus more moderate moving gas having higher temperatures, e.g., about 50° C. to 55° C. Therefore, at high flow rates, the gas has a minimum amount of residence time in the device or passage and thus maximum energy transfer is reduced. At high flow rates, however, the gas has a very short travel time from the device to the patient and thus does not liberate much energy during transit.

The length/volume of the passage or the distance, e.g., about 12 inches, in which the gas travels and the temperature of the warmer, e.g., about 50° C., is such that even if the flow rate is varied the temperature of the insufflation gas delivered to the patient will remain in acceptable levels, e.g., from about 30° C. to 55° C. Therefore, the temperature of the gas prior to the introduction of the gas to the patient will be closer to the temperature of the warmer if the insufflation gas moves through the passage to allow sufficient time for the warmer to transfer heat to the gas to reach thermal equilibrium and also to allow the least amount of time for the gas to lose heat once it's no longer being warmed by the warmer.

For such a device, an optimal flow rate exists for which the delivered gas will be at a maximum temperature upon reaching the patient. For laparoscopic procedures, high and low flow rates are the most common conditions and the device enables the delivery of efficacious gas to the patient under any flow conditions. For example, the distance or volume of the passage and the distance or volume of the connecting tube is such that the insufflation gas regardless of the flow rate, e.g., 0 to 40 L/min, will be warmed by the warmer and heat loss prior to introduction of the gas into the patient will be in acceptable levels, e.g., from about 30° C. to 55° C. The travel distance through the device can be sufficiently long or extended to ensure that at high flow rates, the gas has the maximum energy transfer, however, this should be weighed against competing design factors such as size, weight, cost, added benefit and so forth.

Figure 20:
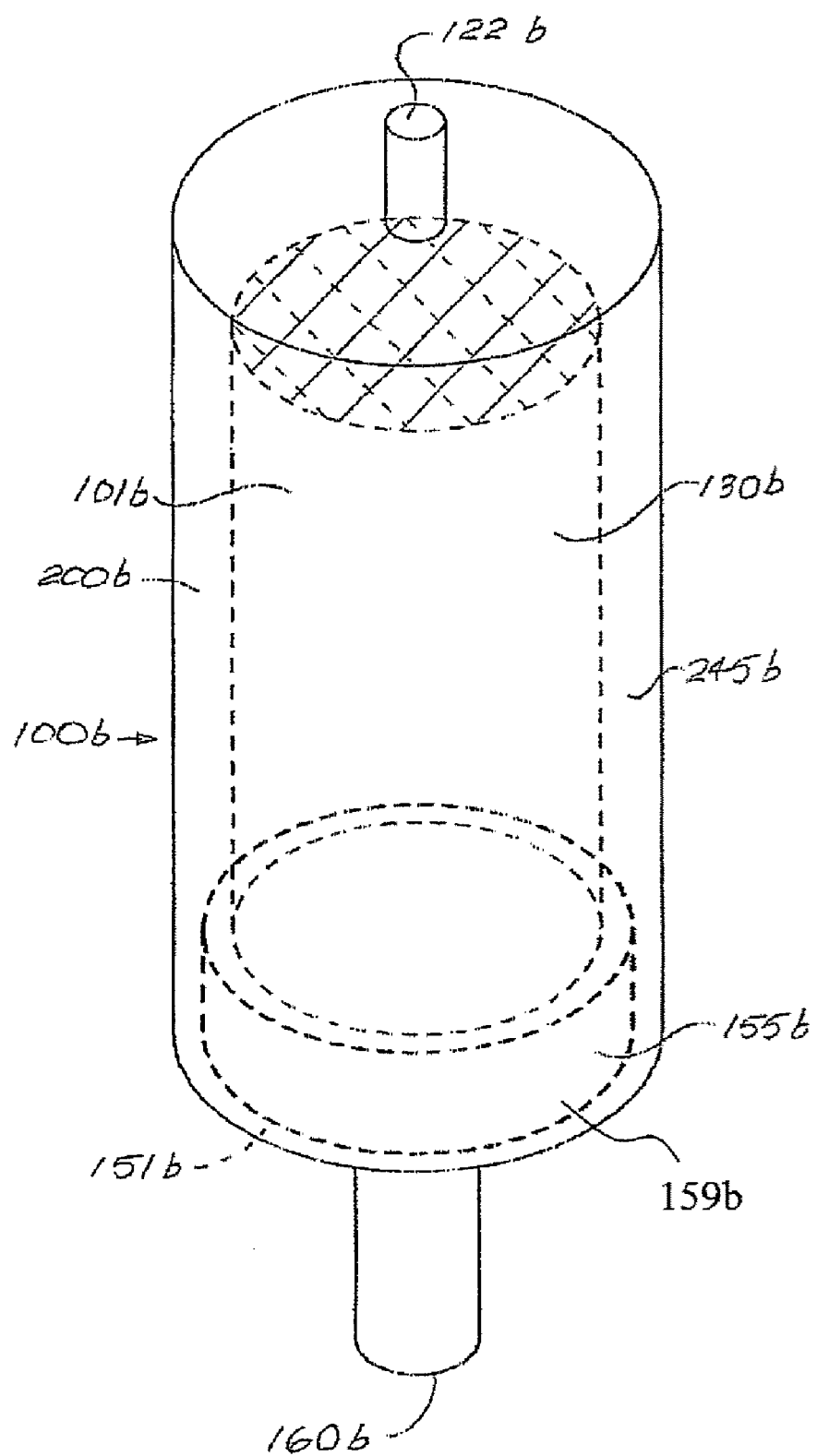
FIG. 20 illustrates one embodiment of an insufflation gas warmer and humidifier including a canister in accordance with one aspect of the present invention.

In one embodiment, as shown in FIG. 20, the warmer and humidifier device includes canisters, pads or pillows 100$b$. The canister 100$b$ attaches or rests upon a surgical table 40. Insufflation gas from the insufflator 50 is supplied to the inlet 160$b$ of the canister 100$b$ and passes through a humidifying portion 151$b$, a holding portion or passage 101$b$ and exits the canister 100$b$ through an outlet 122$b$. The warmer 200$b$ is the outer portion of the canister 100$b$ and includes contents 245$b$. In one embodiment, the passage 101$b$ and humidifier 151$b$ includes a respective contacting surface arranged to allow the transfer of heat from the contents 245$b$ to the respective components. In one aspect, the canister is permeable. In one embodiment, agitating the canister increases the warming reaction within the canister as air mixes with the contents 245$b$ within the canister 100$b$. As such, the insufflation gases from inlet 160$b$ that pass through the humidifying portion 151$b$ are humidified and warmed by the heat from the contents 245$b$ within the canister 100$b$. The flowing insufflation gas within the holding portion 101$b$ are likewise warmed by absorbing the heat from the contents 245$b$ within the canister 100$b$ to deliver humidified and warmed insufflation gas at the outlet 122$b$. In one embodiment, the humidifier 151$b$ includes an absorbent pad 155$b$ with sterile fluid and hydrogen peroxide 159$b$ or another similar chemical to humidify and oxygenate the passing insufflation gas. In one embodiment, a separate filter unit allowing the intake of room air or an oxygenator is provided to oxygenate the passing insufflation gas. In another aspect, the warmer includes heating elements or coils energized to provide sufficient heat to warm the passing insufflation gas to supplement or used in place of the heat transferred by the contents 245$b$.

Figure 21:
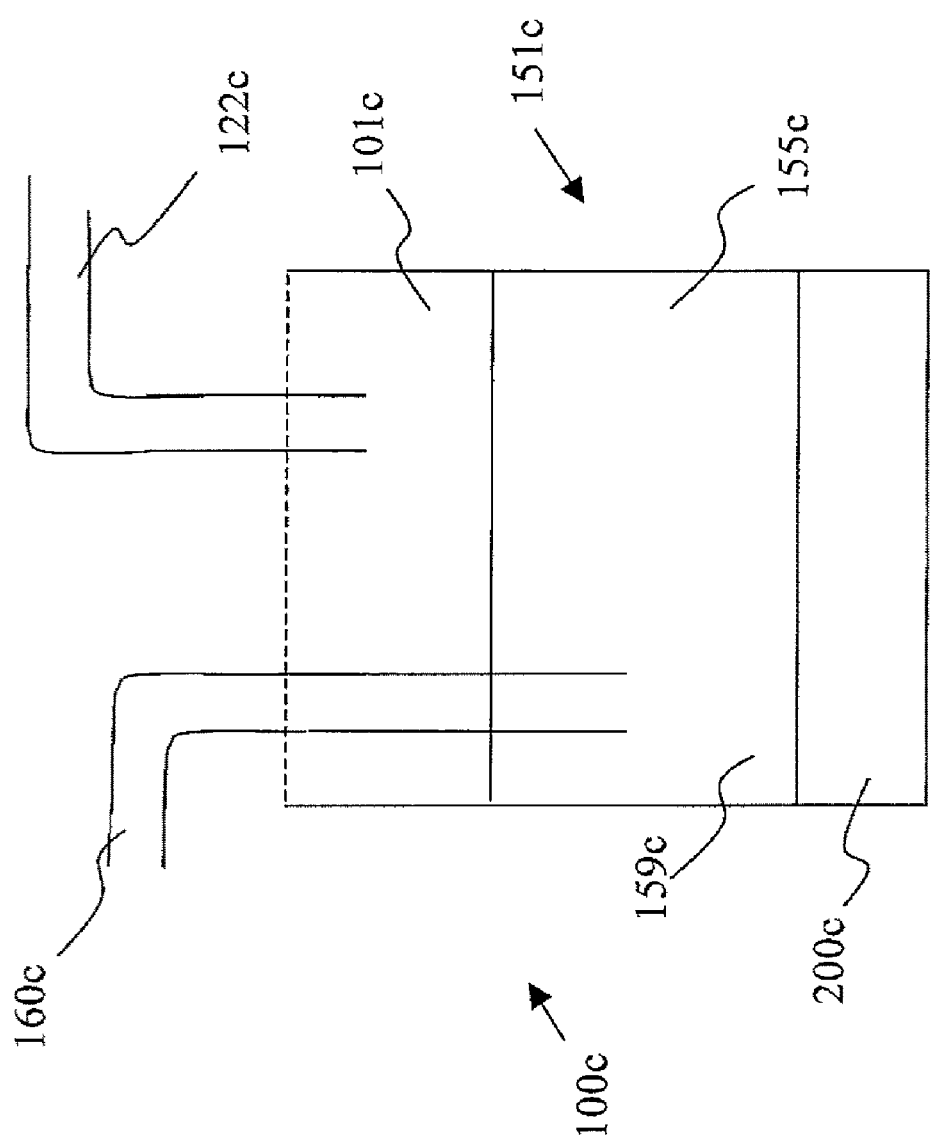
FIG. 21 illustrates one embodiment of an insufflation gas warmer and humidifier including a bubbler in accordance with one aspect of the present invention.
Figure 22:
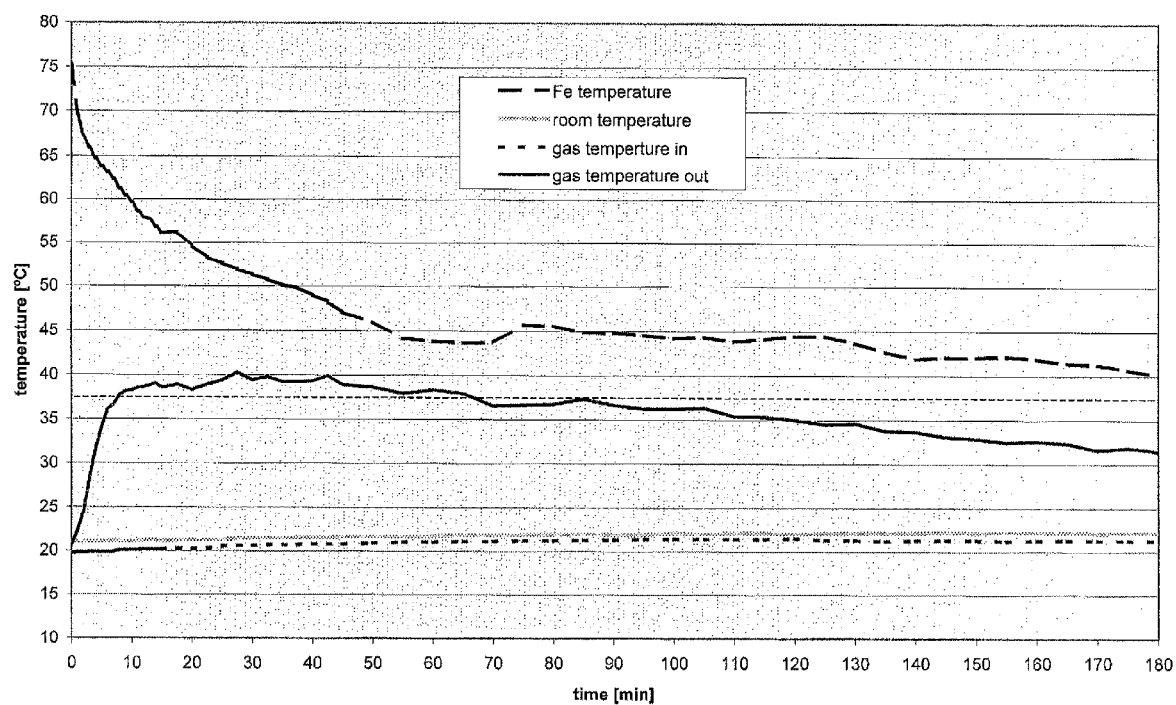
FIG. 22 illustrates exemplary test results of warmed and humidifier insufflation gas in relation to distance, flow rate and temperature relative to one embodiment of an insufflation gas warmer and humidifier in accordance with one aspect of the present invention.

In one embodiment, as shown in FIG. 21, the reservoir 151$c$ includes a bubbler 100$c$. The bubbler 100$c$ attaches or rests upon a surgical table like canister 100$b$. Insufflation gas from the insufflator 50 is supplied to the inlet 160$c$ of the bubbler 100$c$ and exits the bubbler 100$c$ through an outlet 122$c$. A warmer 200$c$ is coupled to the bubbler 100$c$. The warmer 200$c$, in one embodiment, includes wire coils electrically energized to generate heat. The warmer 200$c$, in another embodiment, includes chemical contents when exposed to oxygen generates heat. The generated heat warms the sterile fluid 155$c$ within the reservoir 151$c$. The incoming insufflation gas is expelled or directed into the sterile fluid 100$c$. In one embodiment, hydrogen peroxide 159$c$ or another similar chemical is included with sterile fluid to humidify and oxygenate the insufflation gas. In one embodiment, a separate filter unit allowing the intake of room air or an oxygenator is provided to oxygenate the passing insufflation gas. In one embodiment, the bubbler 100$c$ includes a passage 101$c$ sized and configured to pass the warmed, oxygenated and humidified insufflation gas to the outlet 122$c$ to be introduced into the patient. In another embodiment, the warmer 200$c$ heats the sterile fluid to a specific or range of temperature (or a specific amount of sterile fluid is provided) to ensure that the insufflation gas provided to the patient is a specific or within a specific range of temperatures, humidity and/or oxygenation for corresponding specific or ranges of gas flow rates. FIG. 22 illustrates exemplary test results of insufflation gas warmed and humidified by one embodiment of the above-described bubbler in accordance with one aspect of the present invention.

Figure 23:
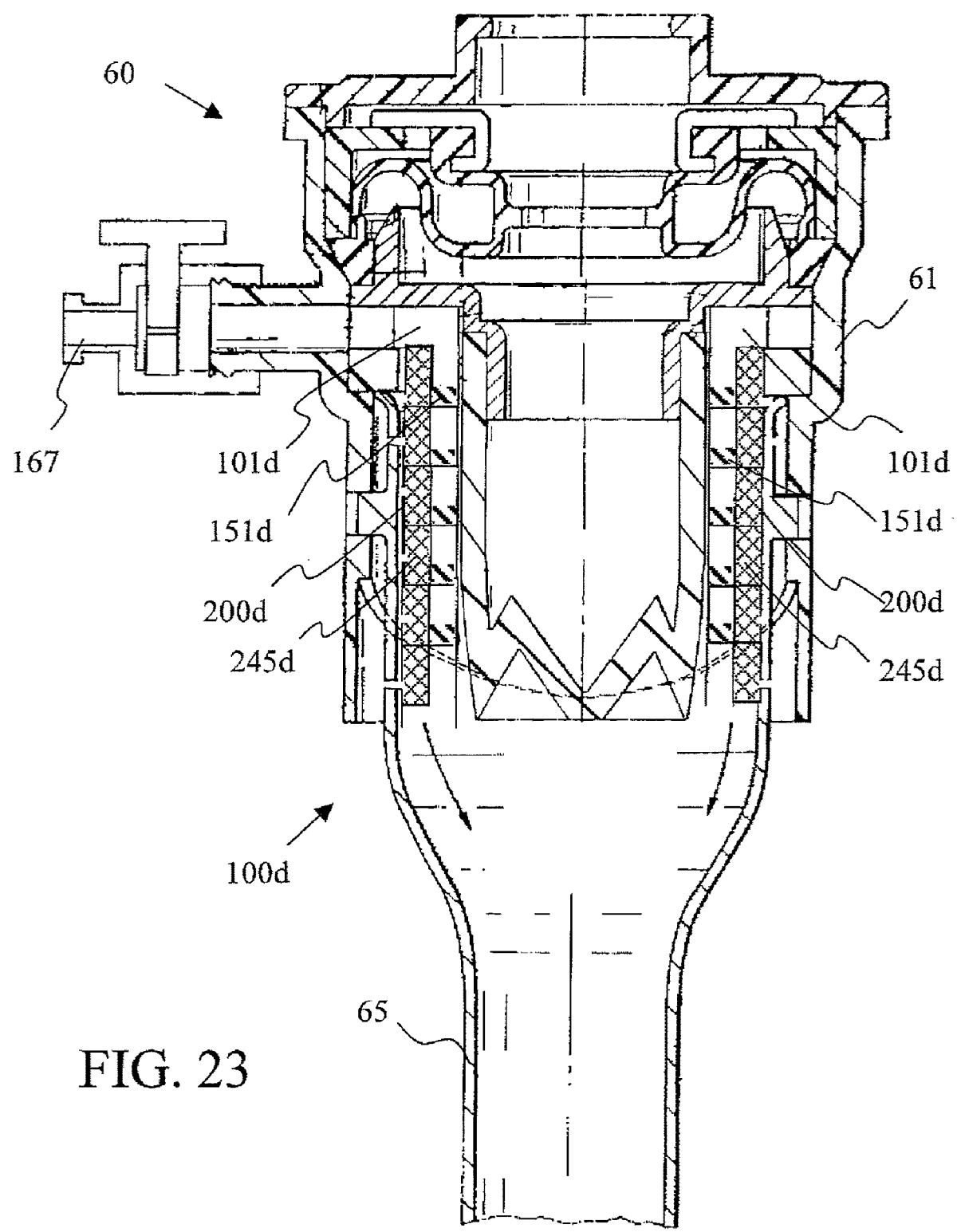
FIG. 23 illustrates one embodiment of an insufflation gas warmer and humidifier included in a valve housing in accordance with one aspect of the present invention.

In one embodiment, the insufflation gas warmer and humidifier device 100$d$ is included within a trocar or valve housing as shown for example in FIG. 23. Insufflation gas from the insufflator 50 is supplied to the inlet 167 of a trocar 60. In one aspect, the trocar includes a valve housing 61 and a cannula 65. The insufflation gas passes through a passage 101$b$, a humidifier 151$d$ and introduced into the cannula 65. In one aspect, the humidifier 151$d$ includes an absorbent pad incorporated within the passage 101$b$ with sterile fluid and, in one embodiment, with an oxygen-introducing chemical. In one aspect, the passage 101$b$ includes a channel that winds around the center of the valve housing. A warmer 200$d$ is on the outer portion of the valve housing 61 and includes contents 245$d$. In one embodiment, the passage 101$d$ and/or humidifier 151$d$ includes a respective contacting surface arranged to allow the transfer of heat from the contents 245$d$ to the respective components. In one aspect, the parts of the outer portion of the valve housing are permeable. As such, the insufflation gases from inlet 167 are humidified, warmed and in one aspect oxygenated and provided to directly to the cannula 65 and thus directly into the patient. Thus, heat, humidity and oxygen loss due to travel distance is eliminated.

In one embodiment, a connecting tube smaller and lighter than the insufflation tubing 55 may used to communicate the insufflation gas from the insufflator 50 and the valve housing 61. In another embodiment, a stop cock may be provided to regulate the incoming insufflation gas or a cutoff or seal to allow use of the valve housing without attaching to an insufflator or insufflation tubing. In one embodiment, a separate filter unit allowing the intake of room air or an oxygenator is provided to oxygenate the insufflation gas. In another aspect, the warmer includes heating elements or coils energized to provide sufficient heat to warm the insufflation gas to supplement or used in place of the heat transferred by the contents 245$d$.

In various embodiments of the present invention, the passage 101, 101$a$-$d$, causes the insufflation gas to wind through the channel such that the insufflation gas provided to the patient is a specific or within a specific range of temperatures, humidity and/or oxygenation for corresponding specific or ranges of gas flow rates. Also, in various embodiments, the warmer and humidifier apparatus is constructed of disposable and inexpensive material. In various embodiments described, the warmer and humidifier apparatus that are closely integrated or incorporated to provide a single unit can be separated such that the warmer, humidifier and/or oxygenator are separate components and vice versa. One or more components such as valves, regulators or the like, in various embodiments, may be inserted between the previously mentioned devices, such as inserting a one-way valve between the inlet and the insufflation gas tubing, to assist in the regulation, maintenance, monitoring, securing and/or protection of connections between devices and the insufflation gas flowing there through.

Accordingly, the present invention provides a simple, lightweight, unobtrusive and inexpensive insufflation gas warmer and humidifier apparatus and methods thereof. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. An insufflation gas warmer apparatus comprising:
   a trocar comprising:
      a valve housing adapted to be coupled to a cannula;
      an inlet arranged to receive insufflation gas; and
      an outlet arranged to be positioned directly in the cannula when the valve housing is coupled to the cannula;
      wherein the valve housing comprises:
         at least one valve positioned in an inner portion of the valve housing, the valve arranged to receive a surgical instrument therethrough;
         a warmer on an outer portion of the valve housing; and
         a passage fluidly coupled to the inlet and the outlet and having at least one channel winding throughout a central portion of the valve housing; and
         wherein the passage includes a heat transfer surface arranged to allow the transfer of heat from the warmer to the passage.

2. The apparatus of claim 1, wherein the trocar further comprises a cannula and wherein the outlet is fluidly coupled to the cannula.

3. The apparatus of claim 1, wherein the valve housing further comprises a humidifier.

4. The apparatus of claim 3, wherein the humidifier comprises an absorbent pad.

5. The apparatus of claim 4, wherein the absorbent pad is incorporated within the passage.

6. The apparatus of claim 4, wherein the absorbent pad includes a sterile fluid.

7. The apparatus of claim 6, wherein the absorbent pad comprises an oxygen-introducing chemical.

8. The apparatus of claim 1, wherein the warmer comprises a chemically reactive agent.

9. The apparatus of claim 1, wherein the valve housing has an outer portion and wherein the outer portion of the valve housing is permeable.

10. An insufflation gas warmer and humidifier apparatus comprising:
    an inlet arranged to receive insufflation gas;
    an outlet;
    a passage connected to the outlet, the passage comprising a contact surface;
    a humidifier connected to the inlet and to the passage and configured to humidify insufflation gas from the inlet and deliver humidified insufflation gas to the passage;
    a permeable canister connected to the inlet and the outlet and encompassing the passage extending through an inner portion of the canister and the humidifier; and
    a warmer including a reactive agent confined within an outer portion of the canister and configured to transfer heat energy to the contact surface of the passage to warm the humidified insufflation gas within the passage.

11. The apparatus of claim 10 further comprising a lightweight connecting tube and a cannula both connected to each other, the connecting tube connected to the outlet.

12. The apparatus of claim 10 wherein the humidifier further includes hydrogen peroxide.

13. The apparatus of claim 10 wherein the humidifier comprises an absorbent pad with sterile fluid.

* * * * *